United States Patent
Angeley et al.

(10) Patent No.: US 10,314,746 B2
(45) Date of Patent: Jun. 11, 2019

(54) LASER EYE SURGERY SYSTEM CALIBRATION

(71) Applicant: OptiMedica Corporation, Santa Ana, CA (US)

(72) Inventors: David Angeley, Charlottesville, VA (US); Bruce Woodley, Palo Alto, CA (US); David Dewey, Sunnyvale, CA (US); Mike Simoneau, Morgan Hill, CA (US); Georg Schuele, Menlo Park, CA (US); Gloria Londono, Charlottesville, VA (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 1385 days.

(21) Appl. No.: 14/069,703

(22) Filed: Nov. 1, 2013

(65) Prior Publication Data
US 2014/0128853 A1    May 8, 2014

Related U.S. Application Data

(60) Provisional application No. 61/722,064, filed on Nov. 2, 2012.

(51) Int. Cl.
*A61F 9/008* (2006.01)
*A61F 9/009* (2006.01)

(52) U.S. Cl.
CPC .......... *A61F 9/00827* (2013.01); *A61F 9/009* (2013.01); *A61F 2009/0087* (2013.01); *A61F 2009/00846* (2013.01); *A61F 2009/00872* (2013.01); *A61F 2009/00887* (2013.01); *A61F 2009/00889* (2013.01)

(58) Field of Classification Search
CPC ............... A61F 9/00827; A61F 9/009; A61F 2009/00846; A61F 2009/0087; A61F 2009/00872; A61F 2009/00887; A61F 2009/00889
USPC ........................................................... 606/4
See application file for complete search history.

(56) References Cited

U.S. PATENT DOCUMENTS

| | | |
|---|---|---|
| 5,459,570 A | 10/1995 | Swanson et al. |
| 5,748,352 A | 5/1998 | Hattori |
| 5,748,898 A | 5/1998 | Ueda |

(Continued)

FOREIGN PATENT DOCUMENTS

| | | |
|---|---|---|
| WO | WO-2006090217 A1 | 8/2006 |
| WO | WO-2011163507 A2 | 12/2011 |

OTHER PUBLICATIONS

Co-pending U.S. Appl. No. 11/328,970, filed Jan. 9, 2006.
Co-pending U.S. Appl. No. 12/510,148, filed Jul. 27, 2009.

*Primary Examiner* — Aaron F Roane
(74) *Attorney, Agent, or Firm* — Johnson & Johnson Surgical Vision, Inc.

(57) ABSTRACT

The amount of energy to provide optical breakdown can be determined based on mapped optical breakdown thresholds of the treatment volume, and the laser energy can be adjusted in response to the mapped breakdown thresholds. The mapping of threshold energies can be combined with depth and lateral calibration in order to determine the location of optical breakdown along the laser beam path for an amount of energy determined based on the mapping. The mapping can be used with look up tables to determine mapped locations from one reference system to another reference system.

16 Claims, 25 Drawing Sheets

(56) References Cited

U.S. PATENT DOCUMENTS

| | | | |
|---|---|---|---|
| 6,053,613 A | 4/2000 | Wei et al. | |
| 6,111,645 A | 8/2000 | Tearney et al. | |
| 7,044,602 B2* | 5/2006 | Chernyak | A61B 3/1015 |
| | | | 351/208 |
| 2008/0281303 A1* | 11/2008 | Culbertson | A61F 2/16 |
| | | | 606/5 |
| 2009/0171327 A1* | 7/2009 | Kurtz | A61F 9/008 |
| | | | 606/6 |
| 2010/0016688 A1* | 1/2010 | Debreczeny | A61B 5/0059 |
| | | | 600/310 |
| 2010/0274228 A1 | 10/2010 | Mrochen et al. | |
| 2011/0190739 A1 | 8/2011 | Frey et al. | |
| 2011/0208180 A1* | 8/2011 | Brannan | A61B 18/1815 |
| | | | 606/33 |

* cited by examiner

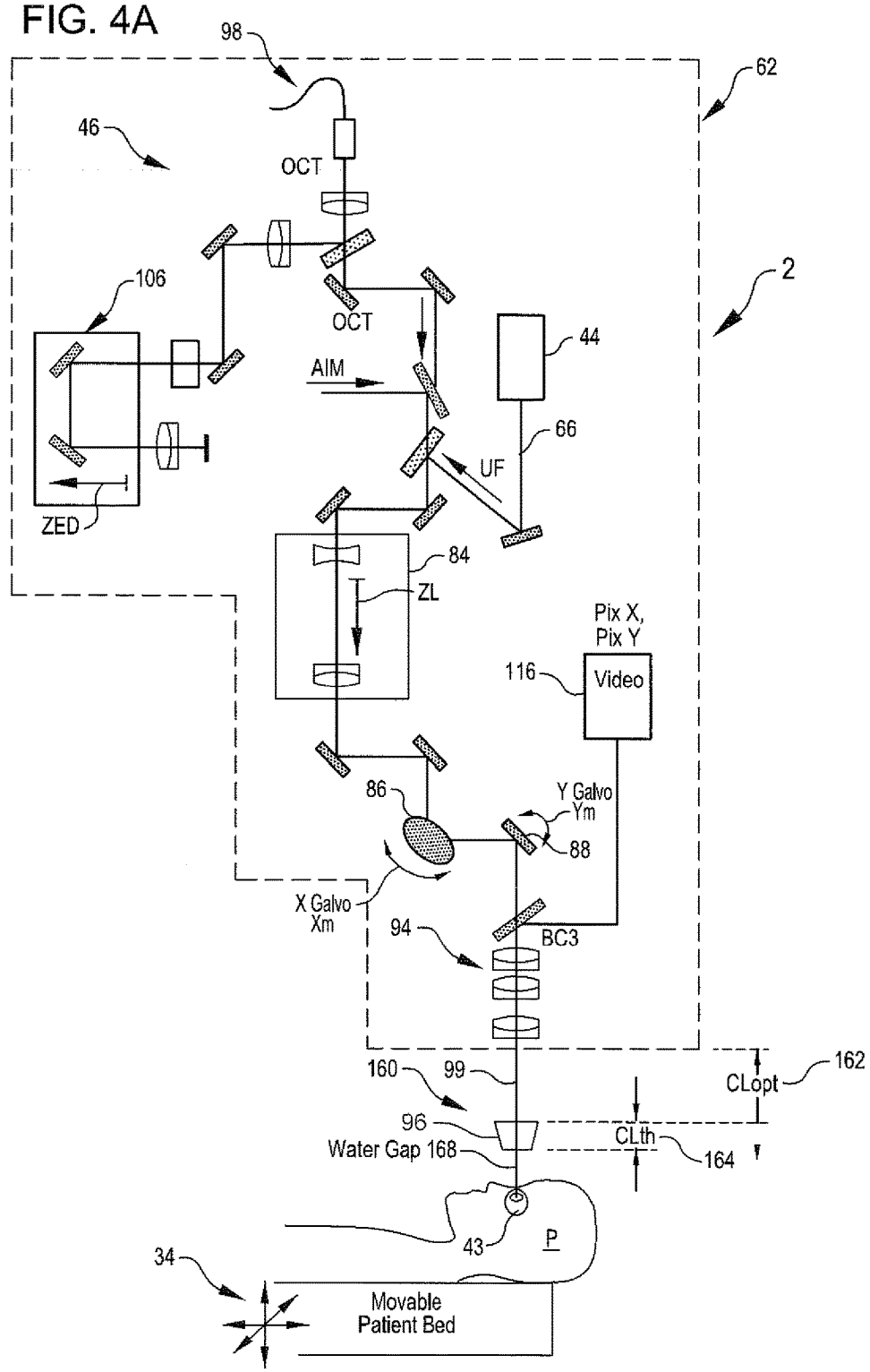

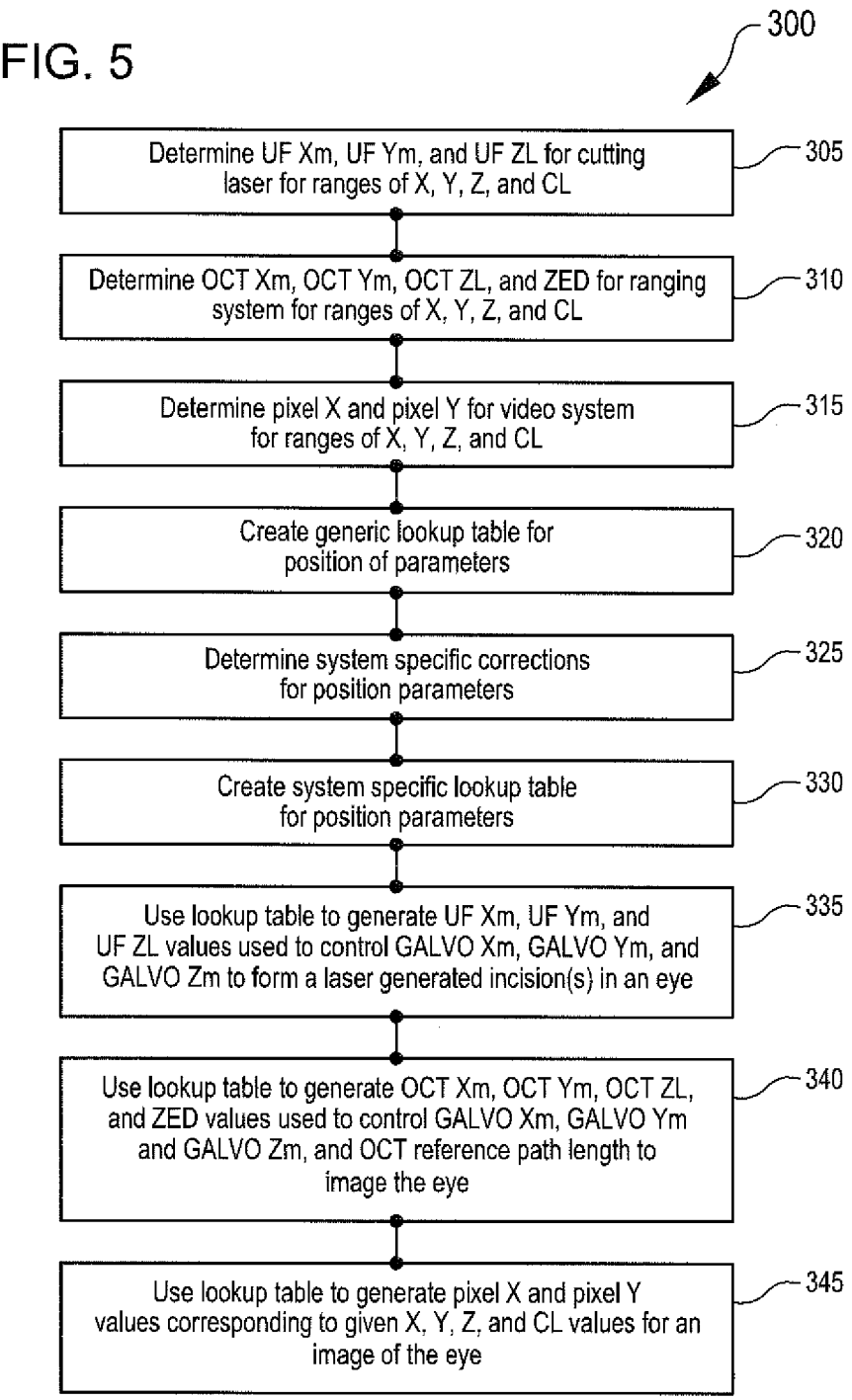

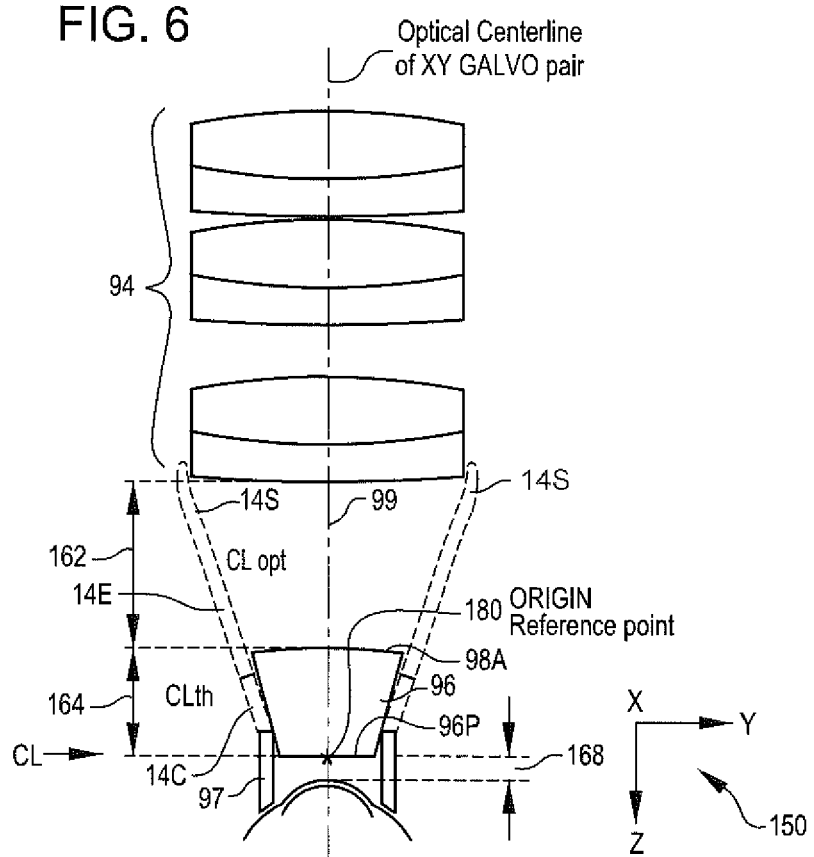

FIG. 7A

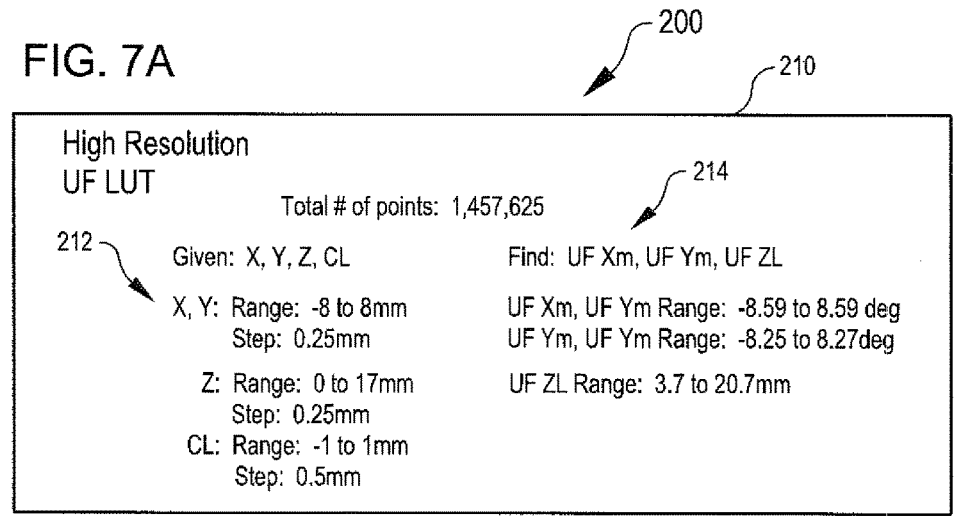

High Resolution UF LUT
Total # of points: 1,457,625

Given: X, Y, Z, CL
X, Y: Range: -8 to 8mm
     Step: 0.25mm
Z: Range: 0 to 17mm
   Step: 0.25mm
CL: Range: -1 to 1mm
    Step: 0.5mm Find: UF Xm, UF Ym, UF ZL
UF Xm, UF Ym Range: -8.59 to 8.59 deg
UF Ym, UF Ym Range: -8.25 to 8.27deg
UF ZL Range: 3.7 to 20.7mm

FIG. 7B

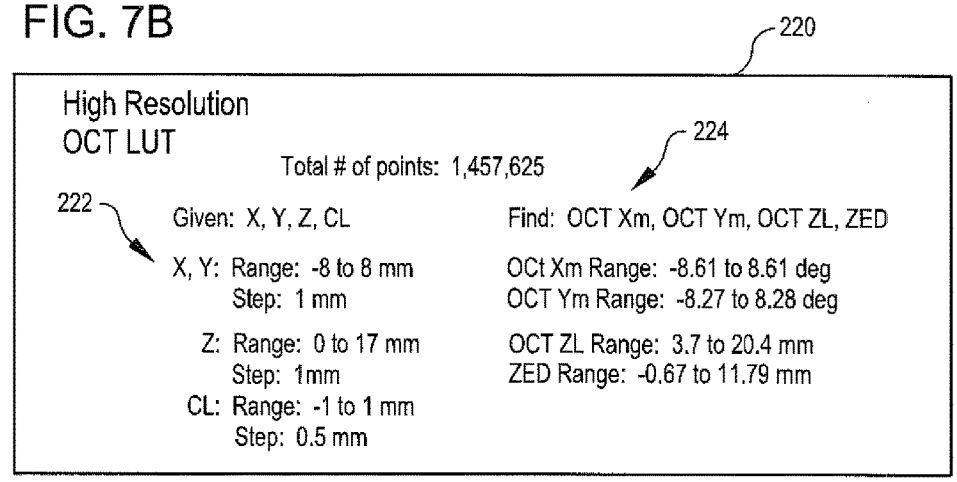

High Resolution OCT LUT
Total # of points: 1,457,625

Given: X, Y, Z, CL
X, Y: Range: -8 to 8 mm
     Step: 1 mm
Z: Range: 0 to 17 mm
   Step: 1mm
CL: Range: -1 to 1 mm
    Step: 0.5 mm Find: OCT Xm, OCT Ym, OCT ZL, ZED
OCt Xm Range: -8.61 to 8.61 deg
OCT Ym Range: -8.27 to 8.28 deg
OCT ZL Range: 3.7 to 20.4 mm
ZED Range: -0.67 to 11.79 mm

FIG. 7C

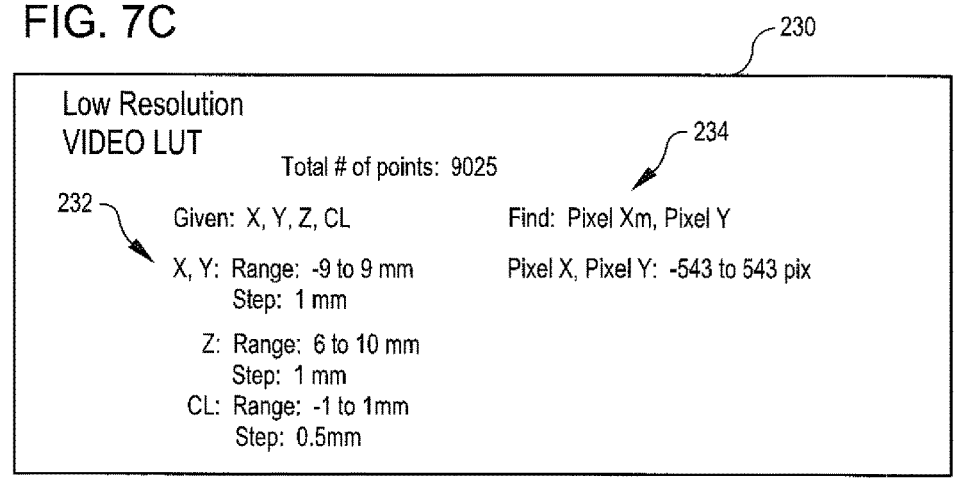

Low Resolution VIDEO LUT
Total # of points: 9025

Given: X, Y, Z, CL
X, Y: Range: -9 to 9 mm
     Step: 1 mm
Z: Range: 6 to 10 mm
   Step: 1 mm
CL: Range: -1 to 1mm
    Step: 0.5mm Find: Pixel Xm, Pixel Y
Pixel X, Pixel Y: -543 to 543 pix

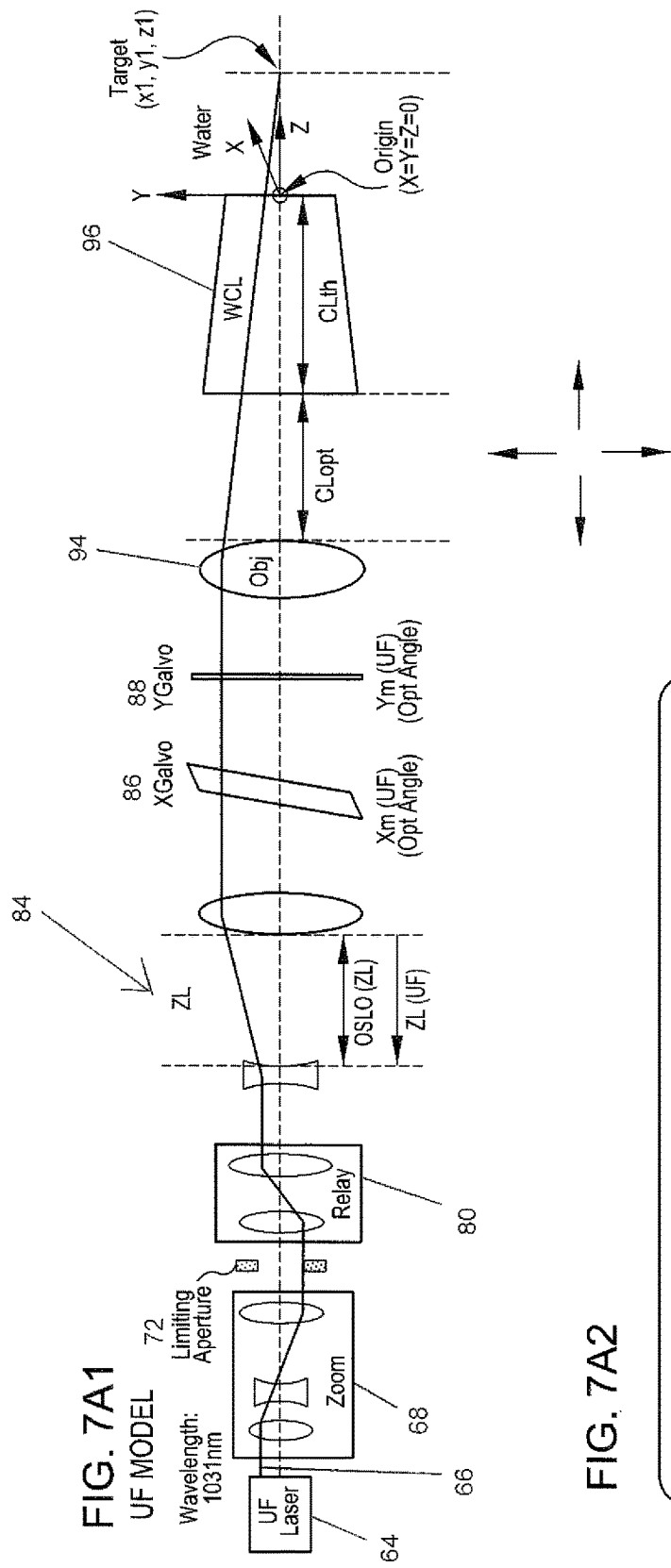

FIG. 7A3

UF LUT,    Xm (UF) [optdeg], Ym(UF) [optdeg], ZL(UF) [mm] @1031nm given X [mm], Y [mm], Z(mm), CLopt [mm], CLth [mm]

| Base Cases | NA | OSLO (ZL) | OPL (UF) | X | Y | Z | CLopt | CLth | Xm (UF) | Ym (UF) | ZL (UF) | ZED (UF) | Dz | Strehl |
|---|---|---|---|---|---|---|---|---|---|---|---|---|---|---|
| 1-Origin | 0.115, | 31.9856, | 1803.1556, | 0.000, | -0.003, | 0.000, | 21.720, | 12.000, | 0.0000, | 0.0000, | 4.3104, | 0.0002, | 0.000, | 0.827 |
| 2-Cornea | 0.128, | 29.3154, | 1809.7800, | 0.000, | -0.002, | 5.000, | 21.720, | 12.000, | 0.0000, | 0.0000, | 6.9806, | 3.3124, | 0.000, | 0.971 |
| 3-Limbus X | 0.138, | 27.1905, | 1813.6048, | 6.000, | -0.000, | 8.000, | 21.720, | 12.000, | 5.8589, | 0.0000, | 9.1055, | 5.2248, | -0.000, | 0.619 |
| 4-Limbus Y | 0.138, | 27.1980, | 1813.7198, | 0.000, | 6.000, | 8.000, | 21.720, | 12.000, | 0.0000, | 5.9588, | 9.0980, | 5.2823, | 0.000, | 0.690 |

UF LUT: ( at Low Low Resolution (3.5mm increments XY, 3mm in Z, 1mm in CLopt, 150mm in CLth ) = 900 entries )

| Xmin | Xmax | Xinc | Ymin | Ymax | Yinc | Zmin | Zmax | Zinc | CLoptmin | CLoptmax | CLoptinc | CLthmin | CLthmax | CLthinc |
|---|---|---|---|---|---|---|---|---|---|---|---|---|---|---|
| -7.00, | 7.00, | 3.5, | -7.00, | 7.00, | 3.5, | 5.00, | 14.00, | 3.0, | 20.72, | 22.72, | 1.0, | 11.85, | 12.15 | 0.15, |

| Step | OSLO (ZL) | OPL(-) | X | Y | Z | CLopt | CLth | Xm (UF) | Ym (UF) | ZL (UF) | ZED (-) | Dz | Strehl | FLAG |
|---|---|---|---|---|---|---|---|---|---|---|---|---|---|---|
| 1. | 29.7342, | 1, | -7.000, | -7.000, | 5.000, | 20.72, | 11.850, | -6.7679, | -7.0116, | 6.5618, | 1, | 0.0020, | 0.01, | 1 |
| 2. | 29.8844, | 1, | -3.500, | -7.000, | 5.000, | 20.72, | 11.850, | -3.3682, | -6.9626, | 6.4116, | 1, | 0.0014, | 0.07, | 1 |
| 3. | 29.9327, | 1, | 0.000, | -7.000, | 5.000, | 20.72, | 11.850, | 0.0000, | -6.9466, | 6.3633, | 1, | 0.0011, | 0.20, | 1 |
| 4. | 29.8844, | 1, | -3.500, | -7.000, | 5.000, | 20.72, | 11.850, | 3.3682, | -6.9626, | 6.4116, | 1, | 0.0014, | 0.07, | 1 |
| 5. | 29.7337, | 1, | -7.000, | -7.000, | 5.000, | 20.72, | 11.850, | 6.7679, | -7.0116, | 6.5623, | 1, | 0.0028, | 0.01, | 1 |

15 Columns → 272

270 → HEADER
271 → BODY

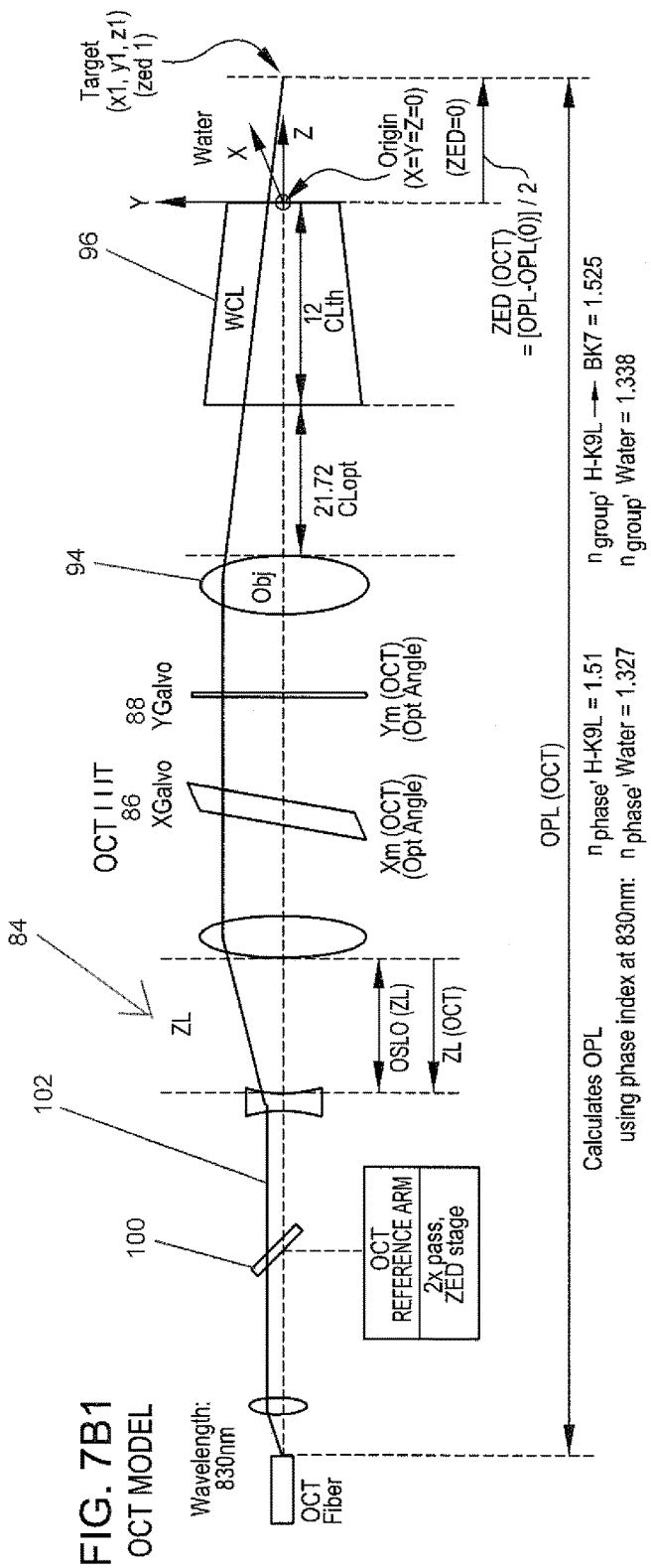

FIG. 7B3

HEADER (273):

| OCT LUT, | | | Xm (OCT) [opt deg], | Ym(OCT) [opt deg], | ZL(OCT) [mm] @830nm using phase index given X [mm], | Y [mm], | Z(mm), | CLopt [mm], | CLth [mm] | | | | | |
|---|---|---|---|---|---|---|---|---|---|---|---|---|---|---|
| Base Cases | NA | OSLO (ZL) | OPL (OCT) | | X | Y | Z | CLopt | CLth | Xm (OCT) | Ym (OCT) | ZL (OCT) | ZED (OCT) | Dz | Strehl |
| 1-Origin | 0.055, | 32.0021, | 960.5331, | | -0.000, | -0.002, | 0.000, | 21.720, | 12.000, | 0.0000, | 0.0000, | 4.2939, | | 0.0001, | 0.001, | 0.984 |
| 2-Cornea | 0.062, | 29.3069, | 967.1728, | | -0.000, | -0.001, | 5.000, | 21.720, | 12.000, | 0.0000, | 0.0000, | 6.9891, | | 3.3200, | 0.000, | 0.995 |
| 3-Limbus X | 0.066, | 27.1787, | 971.0058, | | 6.000, | 0.000, | 8.000, | 21.720, | 12.000, | 5.8735, | 0.0000, | 9.1173, | | 5.2365, | 0.000, | 0.987 |
| 4-Limbus Y | 0.066, | 27.1844, | 971.1205, | | -0.000, | 6.000, | 8.000, | 21.720, | 12.000, | 0.0000, | 5.9713, | 9.1116, | | 5.2939, | 0.000, | 0.979 |

BODY (274):

OCT LUT: ( at Low Low Resolution (3.5mm increments XY, 3mm in Z, 1mm in CLopt, 150mm in CLth ) = 900 entries )

| Xmin | Xinc | Xmax | Ymin | Yinc | Ymax | Zmin | Zinc | Zmax | CLopt | CLth | CLoptmin | CLoptinc | CLoptmax | CLthmin | CLthinc | CLthmax | |
|---|---|---|---|---|---|---|---|---|---|---|---|---|---|---|---|---|---|
| -7.00, | 3.5, | 7.00, | -7.00, | 3.5, | 7.00, | 5.00, | 0.0, | 14.00, | 20.72, | 11.850, | 20.72, | 1.0, | 22.72, | 11.85, | 0.15, | 12.15 | |

| Step | OSLO (ZL) | OPL (OCT) | X | Y | Z | CLopt | CLth | Xm (OCT) | Ym (OCT) | ZL (OCT) | ZED (OCT) | Dz | Strehl | FLAG |
|---|---|---|---|---|---|---|---|---|---|---|---|---|---|---|
| 1. | 29.7333, | 965.6915, | -7.000, | -7.000, | 5.000, | 20.72, | 11.850, | -6.7843, | -7.0237, | 6.5627, | 3.1925, | 0.0034, | 0.64, | 1 |
| 2. | 29.8826, | 965.8475, | -3.500, | -7.000, | 5.000, | 20.72, | 11.850, | -3.3763, | -6.9780, | 6.4134, | 3.2705, | 0.0017, | 0.84, | 1 |
| 3. | 29.9305, | 965.8984, | -0.000, | -7.000, | 5.000, | 20.72, | 11.850, | 0.0000, | -6.9620, | 6.3655, | 3.2960, | 0.0014, | 0.90, | 1 |
| 4. | 29.8826, | 965.8475, | 3.500, | -7.000, | 5.000, | 20.72, | 11.850, | 3.3764, | -6.9780, | 6.4134, | 3.2705, | 0.0018, | 0.84, | 1 |
| 5. | 29.7333, | 965.6915, | 7.000, | -7.000, | 5.000, | 20.72, | 11.850, | 6.7843, | -7.0273, | 6.5627, | 3.1925, | 0.0034, | 0.64, | 1 |

15 Columns — 275

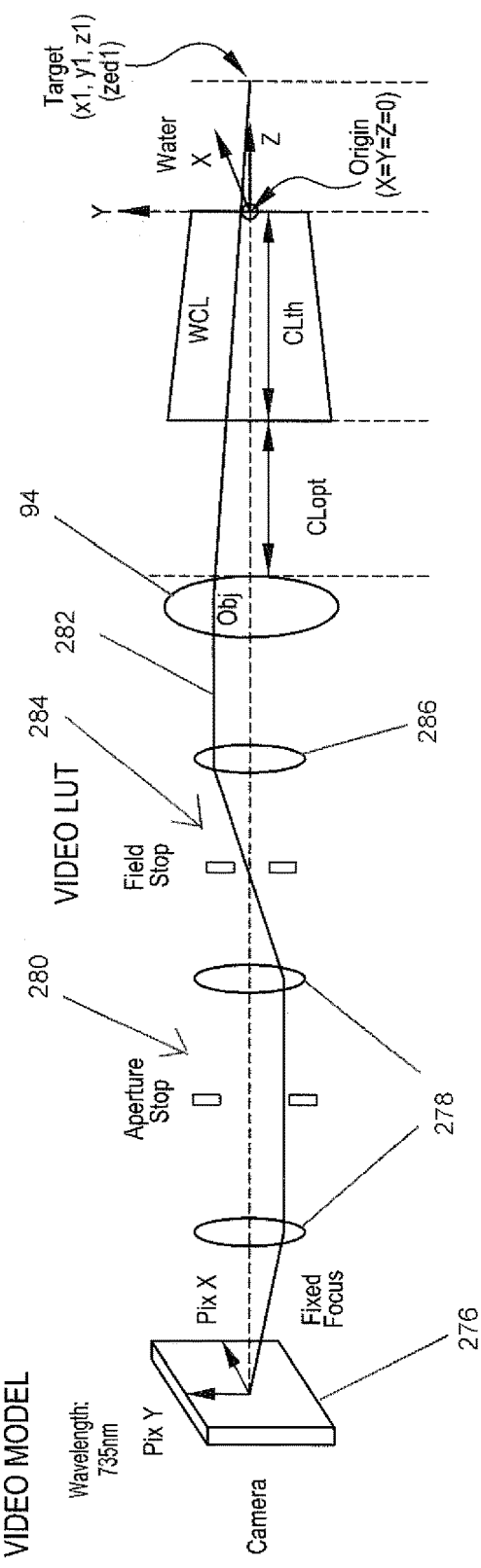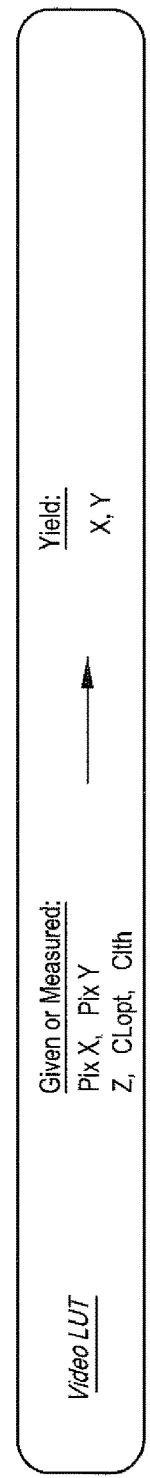
FIG. 7C1
VIDEO MODEL
FIG. 7C2

FIG. 7C3

Video LUT1, 735nm given Z, Y, Z, CLopt, CLth

Base Cases:

| | X | Y | Z | CLopt | CLth | Pix X | Pix Y |
|---|---|---|---|---|---|---|---|
| 1, | 0.000, | 0.000, | 8.000, | 21.720, | 12.000, | 0.00, | 0.00 |
| 2, | 5.000, | 0.000, | 8.000, | 21.720, | 12.000, | 303.10, | 0.00 |
| 3, | 0.000, | 5.000, | 8.000, | 21.720, | 12.000, | 0.00, | 303.10 |

(header 287)

Video LUT: (at low resolution 675 entries)

| Xmin | Xmax | Xinc | Ymin | Ymax | Yinc | Zmin | Zmax | Zinc | CLth |
|---|---|---|---|---|---|---|---|---|---|
| -7.00, | 7.00, | 3.50, | -7.00, | 7.00, | 3.50, | 5.00, | 11.00, | 3.00, | 11.85, |

| CLoptmin | CLoptmax | CLoptinc | CLthmin | CLthmax | CLthinc |
|---|---|---|---|---|---|
| 20.72, | 22.72, | 1.00, | 11.85, | 12.15, | 0.15, |

| Step | X | Y | Z | CLopt | CLth | Pix X | Pix Y | SpotDia (pix) | FLAG |
|---|---|---|---|---|---|---|---|---|---|
| 1, | -7.000, | -7.000, | 5.000, | 20.72, | 11.85, | -418.27, | -418.27, | 0.89, | 1 |
| 2, | -3.500, | -7.000, | 5.000, | 20.72, | 11.85, | -210.53, | -421.06, | 2.79, | 0 |
| 3, | 0.000, | -7.000, | 5.000, | 20.72, | 11.85, | 0.00, | -422.04, | 3.53, | 0 |
| 4, | 3.500, | -7.000, | 5.000, | 20.72, | 11.85, | 210.53, | -421.06, | 2.79, | 0 |
| 5, | 7.000, | -7.000, | 5.000, | 20.72, | 11.85, | 418.27, | -418.27, | 0.89, | 1 |

10 Columns — 289

(body 288)

LASER EYE SURGERY SYSTEM CALIBRATION

CROSS REFERENCE TO RELATED APPLICATIONS

This application claims the benefit of priority to U.S. Provisional Application No. 61/722,064, filed Nov. 2, 2012.

BACKGROUND

The present disclosure relates generally to photodisruption induced by a pulsed laser beam and the location of the photodisruption so as to treat a material, such as a tissue of an eye. Although specific reference is made to cutting tissue for surgery such as eye surgery, embodiments as described herein can be used in many ways with many materials to treat one or more of many materials, such as cutting of optically transparent materials.

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissue may provide a somewhat rougher surface than would be ideal. Pulsed lasers can be used to cut one or more of many materials and have been used for laser surgery to cut tissue.

Examples of surgically tissue cutting include cutting the cornea and crystalline lens of the eye. The lens of the eye can be cut to correct a defect of the lens, for example to remove a cataract, and the tissues of the eye can be cut to access the lens. For example the cornea can be to access the cataractous lens. The cornea can be cut in order to correct a refractive error of the eye, for example with laser assisted in situ keratomileusis (hereinafter "LASIK").

Many patients may have visual errors associated with the refractive properties of the eye such as nearsightedness, farsightedness and astigmatism. Astigmatism may occur when the corneal curvature is unequal in two or more directions. Nearsightedness can occur when light focuses before the retina, and farsightedness can occur with light refracted to a focus behind the retina. There are numerous prior surgical approaches for reshaping the cornea, including laser assisted in situ keratomileusis (hereinafter "LASIK"), all laser LASIK, femto LASIK, corneaplasty, astigmatic keratotomy, corneal relaxing incision (hereinafter "CRI"), and Limbal Relaxing Incision (hereinafter "LRI"). Astigmatic Keratotomy, Corneal Relaxing Incision (CRI), and Limbal Relaxing Incision (LRI), corneal incisions are made in a well-defined manner and depth to allow the cornea to change shape to become more spherical.

Cataract extraction is a frequently performed surgical procedure. A cataract is formed by opacification of the crystalline lens of the eye. The cataract scatters light passing through the lens and may perceptibly degrade vision. A cataract can vary in degree from slight to complete opacity. Early in the development of an age-related cataract the power of the lens may increase, causing near-sightedness (myopia). Gradual yellowing and opacification of the lens may reduce the perception of blue colors as those shorter wavelengths are more strongly absorbed and scattered within the cataractous crystalline lens. Cataract formation may often progresses slowly resulting in progressive vision loss.

A cataract treatment may involve replacing the opaque crystalline lens with an artificial intraocular lens (IOL), and an estimated 15 million cataract surgeries per year are performed worldwide. Cataract surgery can be performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole can be formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

Prior short pulse laser systems have been used to cut tissue, and have been used to treat many patients. The short pulses have a temporal duration that is short enough to provide optical breakdown with plasma formation to cut tissue. These laser systems rely on very accurate placement of the pulses, and a patient interface may be employed to align the laser with tissue. However, the prior patient interfaces can be somewhat cumbersome for users and may result in increased intraocular pressure in at least some instances, and it would be helpful to provide treatments quickly with less reliance on the patient interface. Variability of the tissue location where optical breakdown occurs may result in tissue cutting that may be somewhat rougher than would be ideal in at least some instances. Work in relation to the present disclosure suggests that prior methods and apparatus used to treat materials such as tissue can use in greater amounts of energy than would be ideal and have less accuracy of the location of optical breakdown than would be ideal. Also, exposure to the treatment beam and ultraviolet light resulting from optical breakdown can be greater than would be ideal in at least some instances. Laser cutting of the cataractous lens can result in the formation of gas bubbles that may interfere with the cutting of subsequent pulses, and treatments with gas formation may result in less complete cutting of the lens tissue than would be ideal.

Some of the prior patient interfaces may provide less than ideal results in at least some instances. Prior patient interfaces that place a flat plate on the eye can alter the shape of the cornea and may result in distortion of the cornea and increases in intraocular pressure. Curved patient interfaces that contact the cornea may result in folds of the cornea that may interfere with cutting of tissue, such as lens tissue in at least some instances. Also, the treatment range over which such prior systems can effectively cut tissue with optical breakdown can be less than ideal in at least some instances.

Some of the prior optical coherence tomography (OCT) systems can provide less than ideal results when combined with a patient interface. For example, work in relation with the present disclosure suggests that at least some of the optical surfaces of the prior patient interfaces can interfere with at least some of the prior OCT measurements of the eye in at least some instances.

Thus, improved methods and systems would be helpful for treating materials with laser beams, such as the surgical cutting of tissue to treat cataracts and refractive errors of the eye.

SUMMARY

Embodiments as described herein provide improved treatment of materials such as tissue. The amount of energy to provide optical breakdown in a treatment volume can be varied in accordance with a location of the pulse within the treatment volume, which can provide improved accuracy of the location of optical breakdown along the laser beam path, decreased exposure to the laser beam, decreased gas formation, and decreased ultraviolet light from the optical breakdown. The amount of energy to provide optical breakdown can be determined based on mapped optical breakdown thresholds of the treatment volume, and the laser energy can be adjusted in response to the mapped breakdown thresholds. The mapping of threshold energies can be combined with depth and lateral calibration in order to determine the location of optical breakdown along the laser beam path for an amount of energy determined based on the mapping. In many embodiments, the threshold mapping can be performed before the depth and lateral calibration and the depth and lateral calibration performed based on the mapped threshold energies over the treatment volume. The mapping can be used with look up tables to determine mapped locations from one reference system to another reference system, such as from the eye coordinate reference system to a laser coordinate system reference system comprising one or more movable scanning components of the laser system. The methods and apparatus as described herein can be combined with one or more of many patient interfaces, including patient interfaces that contact the cornea with a flat or curved anterior surface, so as to provide an improved patient treatment.

In many embodiments, a patient interface comprises an optically transmissive structure, such as a lens or a flat plate, which can be placed a distance from the cornea so as to inhibit deformation of the cornea during treatment. The optically transmissive structure placed apart from the cornea may provide improved imaging with OCT or video, and can be combined with the ultrafast laser so as to provide an extended range over which optical breakdown can be produced within a treatment region. In many embodiments, the optically transmissive structure of the patient interface comprises a lens so as to extend the range of optical breakdown treatment within the eye when the lens is spaced apart from the anterior surface of the cornea and coupled to the objective lenses of the laser delivery system.

The improved methods and apparatus for laser calibration can provide improved accuracy of the cutting of tissue, such as cuts into the cornea for refractive treatment of the cornea and access of the cornea for cataract surgery. With refractive cutting of the corneal tissue, the cut may extend at least about eighty percent of the thickness of the cornea, and the improved accuracy of optical breakdown along the laser beam path can provide improved refractive and access cuts to the corneal tissue. The accuracy of cuts within one or more of the structures of the lens can be similarly improved.

In a first aspect, embodiments provide a method of treating an eye. The method comprises mapping a plurality of laser beam focus locations comprising coordinate locations of a laser delivery system. A treatment table is generated, in which the treatment table comprises a plurality of target locations of the eye. The plurality of target locations of the eye is adjusted based on the mapped plurality of laser beam focus locations so as to treat the eye at the plurality of target locations with the laser delivery system.

In another aspect, embodiments provide an apparatus to treat an eye. The apparatus comprises a laser to generate a pulsed laser beam, and an optical delivery system coupled to the laser. A processor is coupled to the laser and the optical delivery system. The processor is configured to generate a treatment table comprising a plurality of target locations of the eye and adjust the plurality of target locations of the eye in response to a mapped plurality of laser beam focus locations.

In another aspect, embodiments provide a method of treating an eye. The method comprises determining a plurality of threshold amounts of laser beam energy to induce optical breakdown at a plurality of laser beam locations. A treatment table is generated comprising a plurality of target locations of the eye. The laser beam pulse energy at the plurality of target locations is adjusted in response to the plurality of threshold amounts.

In another aspect, embodiments provide an apparatus to treat an eye, the apparatus comprises a pulsed laser to generate pulses of light energy and an optical delivery system coupled to the laser. A processor is coupled to the laser and the optical delivery system. The processor is configured to generate a treatment table comprising a plurality of target locations of the eye and adjust the laser beam pulse energy at the plurality of target locations in response to the plurality of threshold amounts.

In another aspect, embodiments provide a method of treating an eye with a laser. The method comprises determining a threshold amount of output pulse energy of the laser to provide optical breakdown within the eye. The output pulse energy of the laser is adjusted below the threshold amount. Optical breakdown is provided within the eye with output pulse energy adjusted below the threshold amount.

In another aspect, embodiments provide an apparatus to treat an eye. The apparatus comprises a laser to generate a plurality of laser beam pulses and an optical delivery system to deliver the plurality of laser beam pulses to a plurality of locations of the eye. A processor is coupled to the laser and the optical delivery system. The processor is configured to determine a threshold amount of output pulse energy of the laser to provide optical breakdown within the eye and adjust the output pulse energy of the laser below the threshold amount in order to provide optical breakdown within the eye.

In another aspect, embodiments provide an apparatus to treat an eye. The apparatus comprises a laser to generate a plurality of laser beam pulses. An optical delivery system comprises a movable lens to focus the plurality of laser beam pulses to a plurality of depth locations of the eye. A patient interface is configured to couple the optical delivery system to the eye. The patient interface comprises an interface lens having an anterior surface and a convexly curved posterior surface. A processor is configured to adjust the movable lens to maintain focus of the laser beam pulses based on measured locations of the interface lens and mapped locations of the eye.

BRIEF DESCRIPTION OF THE DRAWINGS

FIG. 4A shows correspondence among movable and sensor components of the laser delivery system, in accordance with many embodiments;

FIG. 5 shows a method of calibration for a laser system, in accordance with many embodiments;

FIG. 6 shows an eye coordinate reference system referenced to a lower surface of an optically transmissive structure of a patient interface, in accordance with many embodiments;

FIG. 7A shows a look up table summary for an ultrafast laser, in accordance with many embodiments;

FIG. 7A1 shows an optical schematic of the components corresponding to the look up table summary of FIG. 7A;

FIG. 7A2 shows input and output of the look up table as in FIGS. 7A and 7A1;

FIG. 7A3 shows structure and excerpt of a look up table as in FIGS. 7A to 7A2;

FIG. 7B shows a look up table summary for an optical coherence tomography system, in accordance with many embodiments;

FIG. 7B1 shows an optical schematic of the components corresponding to the look up table summary of FIG. 7B;

FIG. 7B2 shows input and output of the look up table as in FIGS. 7B and 7B 1;

FIG. 7B3 shows structure and excerpt of the look up table as in FIGS. 7B to 7B2;

FIG. 7C shows a look up table summary for a video camera, in accordance with many embodiments;

FIG. 7C1 shows an optical schematic of the components corresponding to the look up table of FIG. 7C;

FIG. 7C2 shows the input and output of the look up table as in FIGS. 7C and 7C1;

FIG. 7C3 shows structure and excerpt of the look up table as in FIGS. 7C to 7C2;

DETAILED DESCRIPTION

Figure 1:
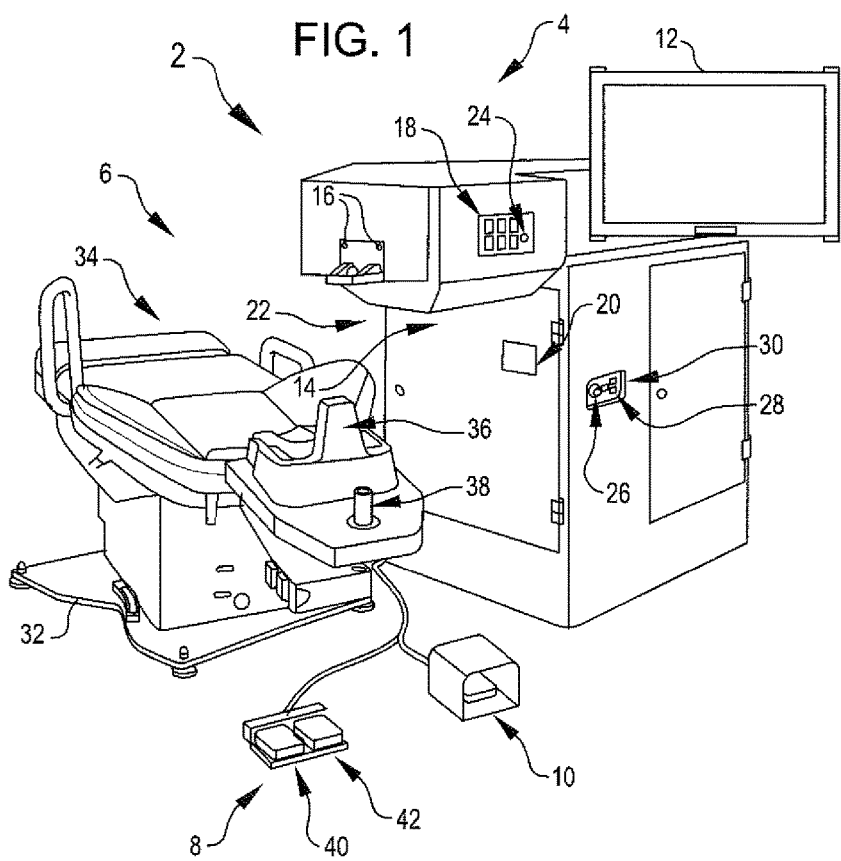
FIG. 1 shows a perspective view showing a laser eye surgery system, in accordance with many embodiments.

Methods and systems related to laser eye surgery are disclosed. In many embodiments, a laser is used to form precise incisions in the cornea, in the lens capsule, and/or in the crystalline lens nucleus. Although specific reference is made to tissue retention for laser eye surgery, embodiments as described herein can be used in one or more of many ways with many surgical procedures and devices, such as orthopedic surgery, robotic surgery and microkeratomes.

The embodiments as describe herein are particularly well suited for treating tissue, such as with the surgical treatment of tissue. In many embodiments, the tissue comprises an optically transmissive tissue, such as tissue of an eye. The embodiments as described herein can be combined in many ways with one or more of many known surgical procedures such as cataract surgery, laser assisted in situ keratomileusis (hereinafter "LASIK"), or laser assisted subepithelial keratectomy (hereinafter "LASEK").

Methods and systems related to laser treatment of materials and which can be used with eye surgery such as laser eye surgery are disclosed. A laser may be used to form precise incisions in the cornea, in the lens capsule, and/or in the crystalline lens nucleus, for example. The embodiments as described herein can be particularly well suited for decreasing the amount of energy to the eye and increasing the accuracy of the cutting of the material such as tissue, for example.

The present disclosure provides methods and apparatus for providing adjustment to compensate for variations in disposable elements and other attachments, tolerances in hardware and alignment, and patient anatomy. The methods and apparatus may comprise a software look up table (hereinafter "LUT") embodied in a tangible medium. The LUT may comprise a map of locations of the cutting volume in order to adjust the control of actuators that direct the ranging (target detection) and the cutting modalities. A baseline LUT can be generated for a generalized system using optical based rules and physics, detailed modeling of components, and anchoring (one time) to a finite data set as described herein. The expected variations can be reduced into a set of finite and manageable variables that are applied to modify the tables subsequent to the original generation of the tables. For a constructed system having constructed components with manufacturing tolerances, fine tuning and modification of the LUTs can be achieved through simple modifications of the tables based on individual system and automated measurements. These individualized measurements of a constructed system can be applied to variations due to one or more of: tool-to-tool variation, tool to itself variation (for example align variations), output attachment variations (for example disposable contact lenses), or patient to patient (for example individual patient anatomy), and combinations thereof, for example.

In many embodiments, one or more of the following steps can be performed with the processor and methods as described herein. For example, baseline LUT generation can be performed comprising mapping and position detection in order to provide actuator commands to evaluate system output performance. A baseline transfer function can be generated for a patient coordinate reference system such as XYZ to detect actuators of the system, for example. Baseline LUT generation can be performed to map cutting to actuators. A transfer function can be generated for XYZ to cutting actuators, for example. Baseline LUTs (transfer functions) can be generated via model (ray trace), data, or a combination, for example. The baseline LUTs can be modified given variations in the system, disposable, eye, application, for example. The baseline LUT modification may comprise an adjustment to the baseline LUT, for example. The baseline LUT modification may comprise a software (hereinafter "SW") adjustment to compensate for hardware (hereinafter "HW") variations, for example. The LUT modification as described herein can extend surgical volume, so as to treat the cornea, the limbus and the posterior capsule, either in lateral extent, axial extent, and resolution, for example. The LUT methods and apparatus can enable switching in tools for calibration and other optical components to accessorize—output attachments, for example. The LUT can be set up so that the system is capable of measuring location of attachments at two surfaces and then can accurately place cuts in targeted material volume based on modifying the baseline LUT using this the locations of the two surfaces, for example. The LUTS can provide more cuts ranging from lens, capsule, corneal incisions for cataract, cornea flaps, for example. The different sub-systems as described herein can have separate LUTS, which can be combined with calibration process as described herein, for example.

Alternatively, or in combination, the same sub-system can be used for both ranging and cutting, for example. The ultrafast (hereinafter "UP") system can be used at a low power level to find surfaces and then used at high power for cutting, for example. The LUTs can be used such that the location mode differs from the cutting mode. For example, the cut locations can differ based on changes with power level. The cut location may not occur at focus, for example when the energy per pulse substantially exceeds the threshold amount of energy, for example.

In many embodiments, the LUTs of the methods and apparatus as described herein follow these principles. The baseline LUT can generated by ray tracing and data anchoring using specific tooling, for example. In many embodiments, each optically transmissive structure of the patient interface, for example a lens, is read by the system to determine its thickness and location. These numbers can be used to modify the LUTS to attain <100 um accuracy, for example.

In many embodiments, the LUTs of the methods and apparatus as described herein are also modified to account for alignment tilts, contact lens mounting, contact lens variations so as to achieve <100 um accuracy on cuts, for example. In many embodiments, a bubbles in plastic flatness test with the calibration apparatus as described herein generates offset and tilt adjustments of baseline UF LUT.

In many embodiments, the baseline component specifications may be less than ideal for delivering an appropriate system performance, and the final performance can be refined using SW corrections and factors based on the components of the individual system which can be determined from optically-grounded data-anchored baseline LUTs further modified for enhanced performance, for example.

A feedback loop can be used to build the enhanced or modified LUTs for the individual laser system, for example. The feedback methods and apparatus as described herein can allow SW adjustments based on LUTs and other SW factors that may not be corrected with hardware alignment, for example.

The LUTs and the methods and apparatus configured to modify the look up tables so as to enhance system performance can provide an improvement within the 3D surgical volume as described herein. The methods and apparatus as described herein can provide improved surgery for more patients with a level of high performance. The methods and apparatus as described herein can provide high performance using off-the-shelf components, such as high volume low cost components, such that the surgical procedures as described herein can be available to many patients.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
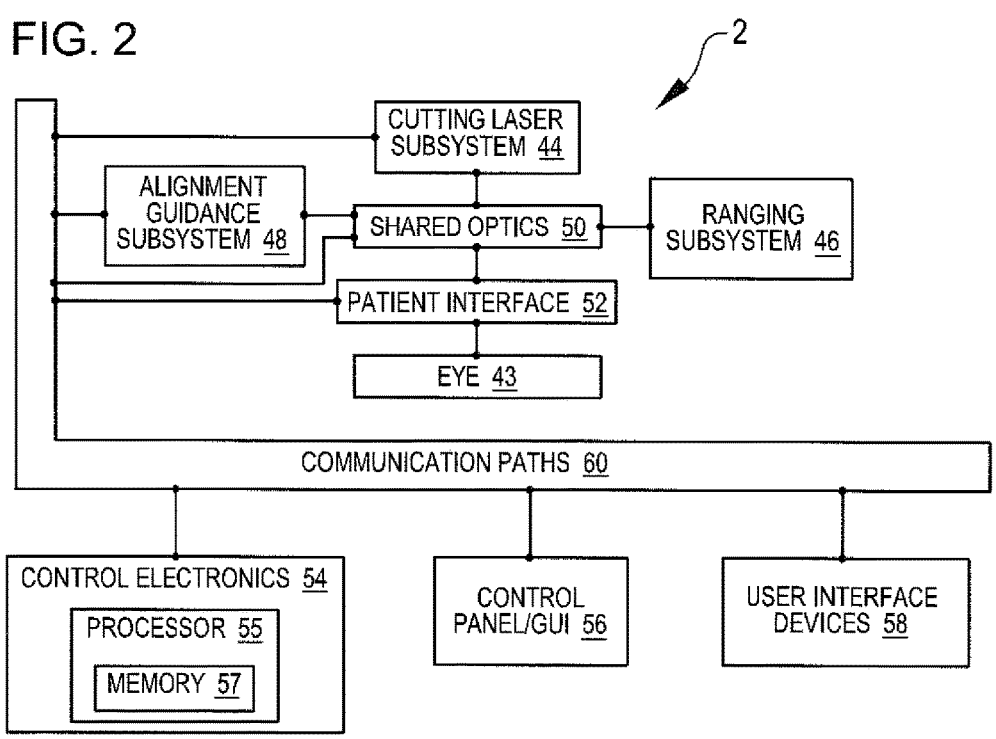
FIG. 2 shows a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea 43C, a lens 43L and an iris 431 as depicted in FIG. 3. The iris 431 defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes OCT imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
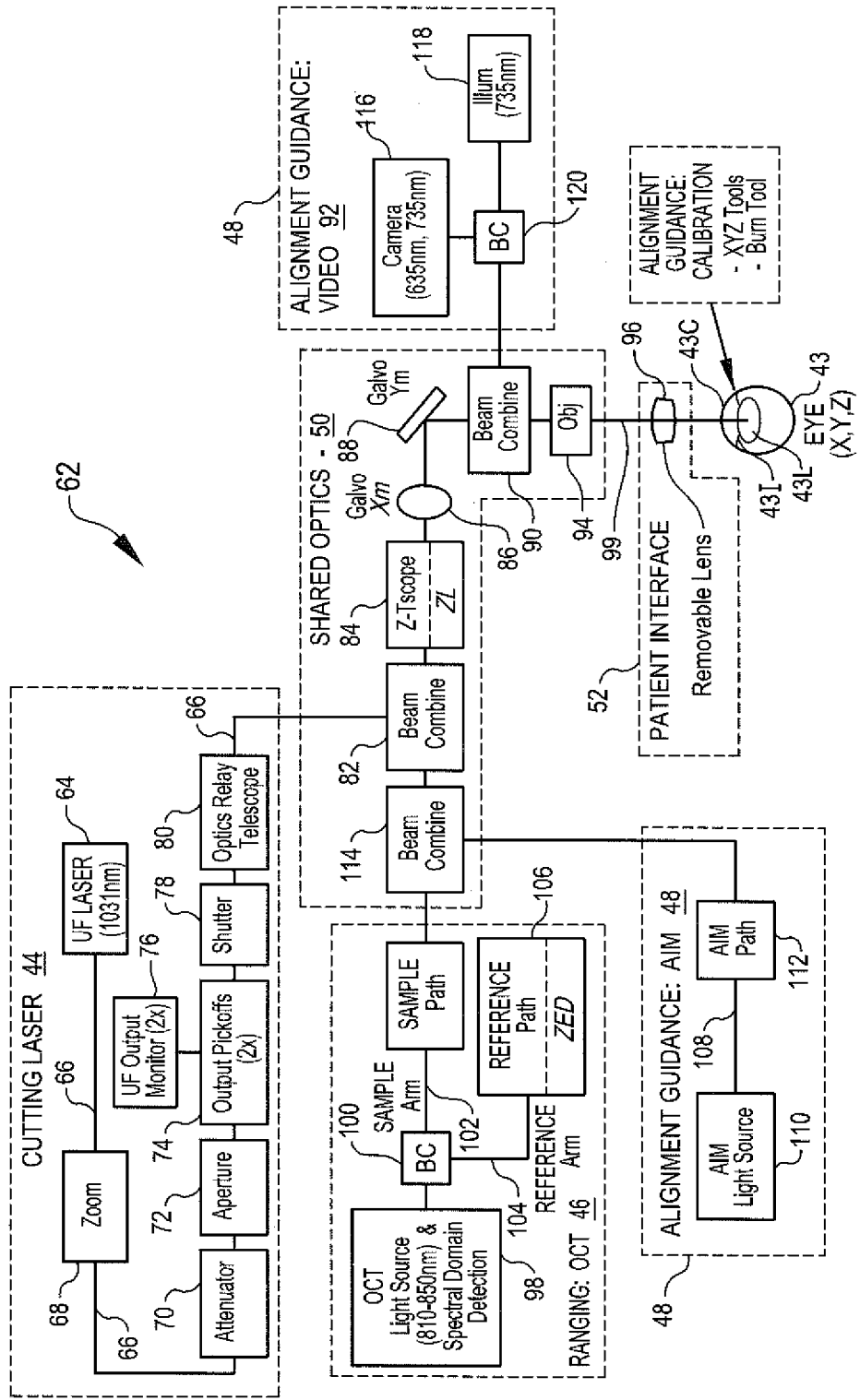
FIG. 3A shows a simplified block diagram illustrating the configuration of an optical assembly of a laser eye surgery system, in accordance with many embodiments.

FIG. 3A is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the XY galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a Z-scan device for scanning the focus point of the laser-pulse beam 66 in the patient's eye 43. The Z-telescope 84 can be controlled automatically and dynamically by the control electronics 54 and selected to be independent or to interplay with the X- and Y-scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66.

The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-scan device 86 and the Y-scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3A, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3A includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the OF laser pulse beam 66 will be focused on the lens capsule and cornea at all points of the desired opening. Imaging modalities and techniques described herein, such as for example, OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
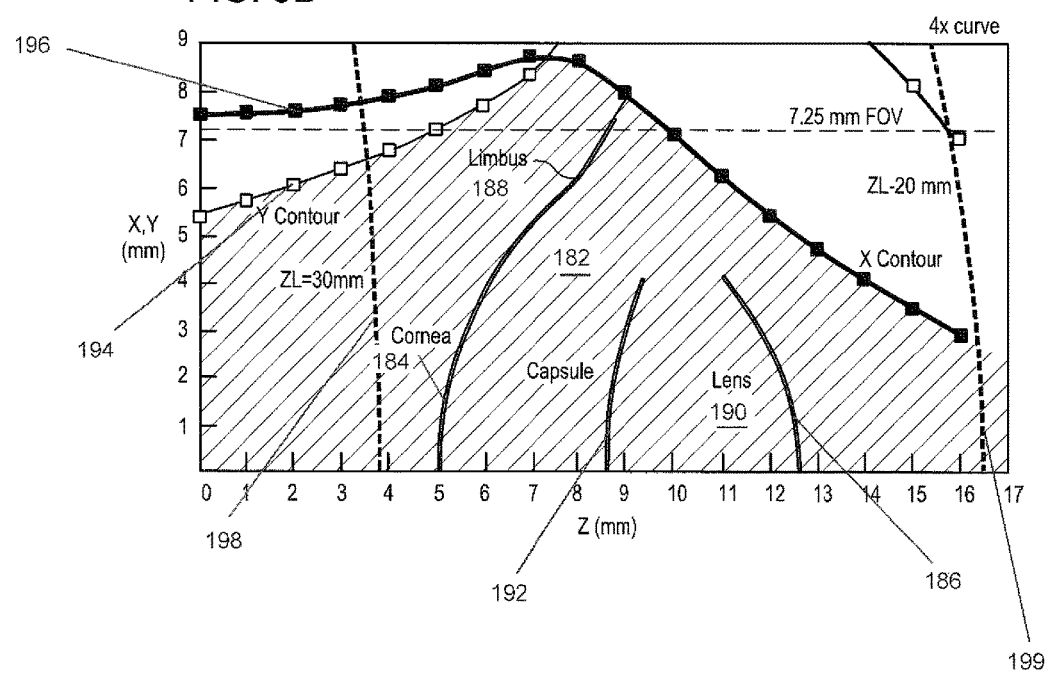
FIG. 3B shows a mapped treatment region of the eye comprising the cornea, the posterior capsule, and the limbus, in accordance with many embodiments.

FIG. 3B shows a mapped treatment region 182 (hatched area) of the eye comprising the cornea 184, the posterior capsule 186, and the limbus 188. The treatment region 182 can be mapped with computer modeling, for example ray tracing and phased based optical modeling to incorporate factors such as laser beam quality, pulse width, system transmission, numerical aperture, polarization, aberration correction, and alignment. The treatment volume 182 is shown extending along the Z-axis from the posterior surface of the optically transmissive structure of the patient interface a distance of over 15 mm, such that the treatment volume 182 includes the cornea 184, and the lens 190 in which the treatment volume of the lens 190 includes the anterior capsule 192, the posterior capsule 186, the nucleus and the cortex. The treatment volume 182 extends laterally from the center of the cornea 184 to beyond the limbus 188. The lateral dimensions of the volume 182 are defined by a Y contour 194 anterior to the limbus 188 and by an X contour 196 posterior to the limbus 188. The treatment volume 182 shown can be determined by a person of ordinary skill in the art based on the teachings described herein. The lateral positions of predicted optical breakdown for ZL fixed to 30 mm 198 and ZL fixed to 20 mm 199 are shown. These surfaces that extend transverse to the axis 99 along the Z-dimension correspond to locations of optical scanning of the X and Y galvos to provide optical breakdown at lateral locations away from the axis 99. The curved non-planar shape of the scan path of optical breakdown for ZL-30 mm 198 and ZL-20 mm 199 can be corrected with the mapping and LUTs as described herein. The curved shape of the focus can be referred to as a warping of the optical breakdown depth and the LUTs can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region 182 is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and LUTs as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume 182 may optionally be adjusted with mapping based on measurements of a constructed system as described herein.

Figure 3C:
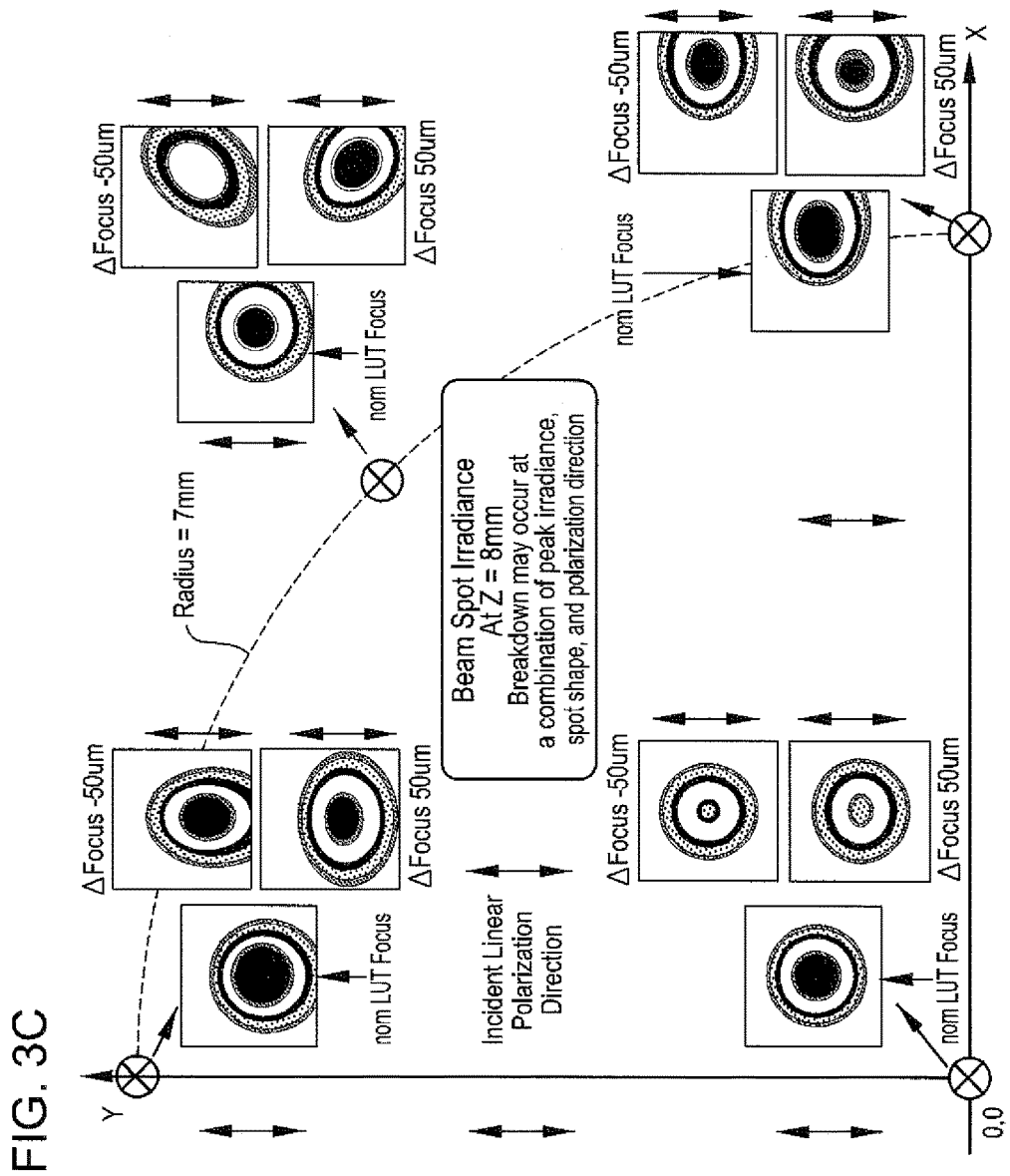
FIG. 3C shows mapped changes in beam focus for locations of the mapped treatment region, in accordance with many embodiments.

FIG. 3C shows mapped changes in beam focus for locations of the mapped treatment region 182. The locations of optical breakdown can be mapped at a plurality of depths and lateral locations so as to map the location of optical breakdown over the treatment volume 182. The laser beam spot irradiance can be determined with computer modeling software, for example. The location of optical breakdown can be determined based on the laser beam spot irradiance pattern, such that the location of optical breakdown along the laser beam path can be determined. The optical breakdown for a given set of laser parameters such as beam quality and pulse width can occur at a combination of one or more of peak irradiance, spot shape, or polarization direction, for example. The mapped beam shape can be at planes of a treatment volume, for example. The mapped focus can be determined with commercially available optical modeling software based on the teachings described herein. The mapped changes in beam focus may comprise a mapped focus at a depth of 8 mm on the axis of the coordinate reference system, for example. Similar mapping can be performed at additional depths as described herein. The focused beam profile can be determined for the nominal location and +50 um and −50 um, so as to evaluate the irradiance pattern to determine the location of optical breakdown. The focused beam profile can be determined at several locations along the plane away from the axis. For example, the beam profile can be determined at locations along a radius of the treatment volume, such as at the 0, 45 and 90 degree locations along a 7 mm circle, for example.

In many embodiments, the laser beam output energy comprises a value substantially above the amount required near the center of the treatment volume, for example four times the amount required at the center, so as to provide optical breakdown near the edges of the treatment volume, and the location of optical breakdown can be determined based on the beam spot irradiance profile and the output energy of the laser. This mapping can be performed initially in software, and may optionally be further refined based on mapping measurements of a constructed system as described herein.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 86 capable of moving an angular amount Xm, and the Y galvo minor 88 capable of moving an angular amount Ym. The movable components of the OCT system may comprise the movable OCT reference arm configured to move the reference path 106 a distance ZED. The sensor components of the laser system may comprise the video camera 116 having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 96 is separated from the cornea with gap 168 extending between the lens and the vertex of the cornea, such that the posterior surface of the contact lens 96 contacts a solution comprising saline or a viscoelastic solution, for example.

Figure 4B:
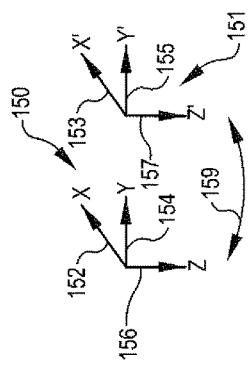
FIG. 4B shows mapping of coordinate references from an eye space coordinate reference system to a machine coordinate reference system, in accordance with many embodiments.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example. In many embodiments the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the Z-telescope lens capable of moving distance ZL. The dimension 153 may correspond to movement of the X galvo mirror 86 capable of moving an angular amount Xm, and the dimension 155 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the Z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the Z-telescope lens capable of moving the distance ZL, for example. In many embodiments, the locations of the components of the laser system 2 are combined when in order to map the plurality of machine coordinate reference systems to the coordinate reference system 150 of eye 43.

In many embodiments, the eye coordinate reference system 150 is mapped from an optical path length coordinate system to physical coordinates of the eye based on the index of refraction of the tissues of the eye. An example is the OCT ranging system where measurements are based on optical thicknesses. The physical distance can be obtained by dividing the optical path length by the index of refraction of the material through which the light beam passes. Preferably the group refractive index is used and takes into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X and Y directions and departure from the telecentric condition occurs due to the axial location of the galvo mirrors, a distortion of the optical path length is realized. This is commonly known as fan error and can be corrected for either through modeling or measurement.

As one or more optical components and light sources as described herein may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both the phase and group index can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 nm. The group refractive index of 1.339 differs on the order of 1% for the OCT beam wavelength and spectral bandwidth. A person of ordinary skill in the art can determine the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

Figure 4C:
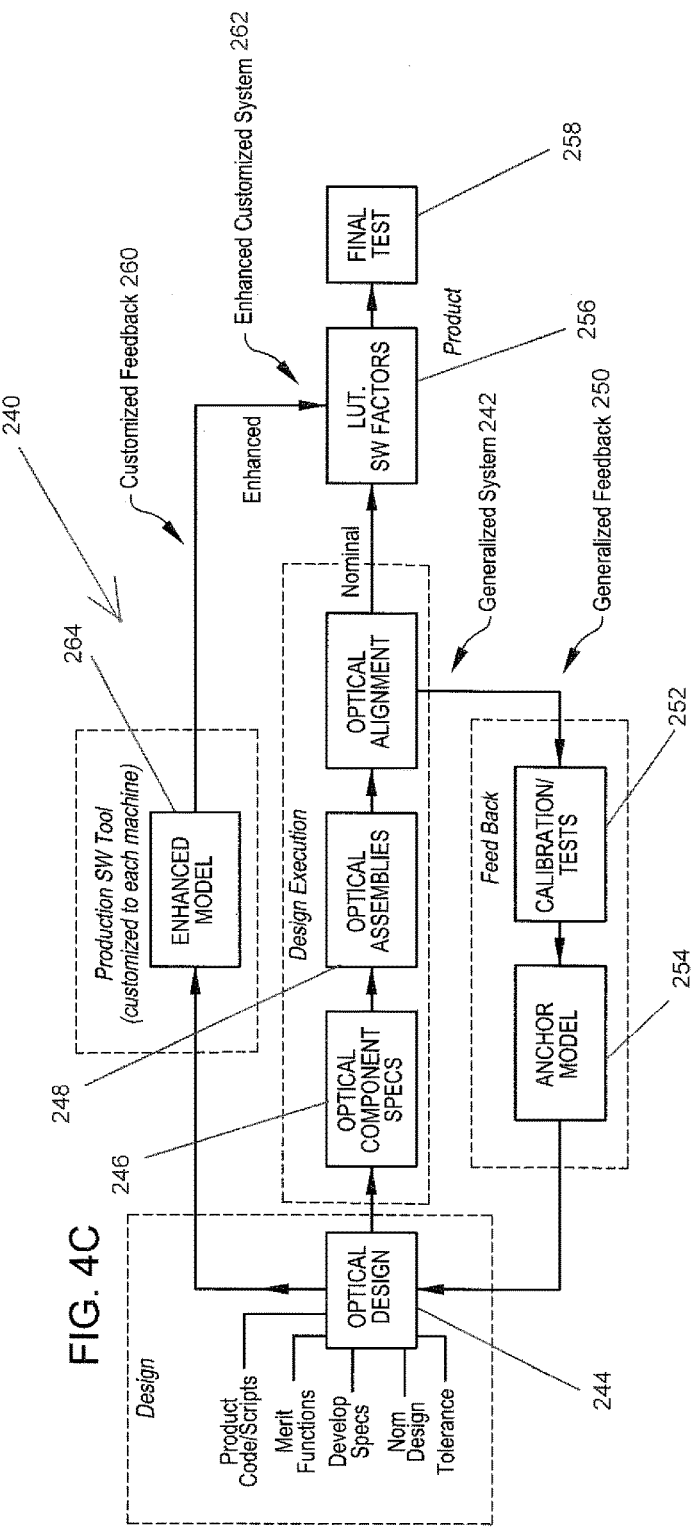
FIG. 4C shows a feedback loop to adjust look up table calibration mapping from a generalized system to a specific individual constructed system based on measurements of the individual constructed system, in accordance with many embodiments.

FIG. 4C shows a feedback loop 240 to adjust LUT calibration mapping from a generalized system having nominal values to a specific individual constructed system based on measurements of the individual constructed system. The system 2 may comprise a generalized system 242 based on optical schematics and components. The generalized system may comprise an optical design 244 as described herein, which can be associated with one or more of product code and scripts, merit functions, optical specifications, a nominal system design of the components and locations, and tolerances associated with the nominal system design components and locations. In the execution of the system design, the optical design 244 is output as optical components and specifications 246, which can be used to configured optical assemblies 248. The optical assemblies 248 and components 246 are aligned. The generalized system design can be further improved with feedback 250. The feedback 250 of the generalized system design may comprise calibration tests 252 and optical modeling 254 that are used to further improve and modify the optical design 244. For example, a system can be constructed based on the nominal design and information from the nominal design fed back to the optical design 244 based on calibration and testing 252, such as tolerances of components and range of treatment. The nominal design of the general system can be used to generate a generalized LUT based on the nominal design. The nominal LUTs and SW factors 256 can be used to produce a final production system, and the final production system can undergo final test procedures 258.

In accordance with many embodiments, an enhanced customized system 2 can be constructed based on the customized feedback path 260 so as to provide a customized system 262. While the customized system 262 can be provided in many ways, in many embodiments a production SW tool is used to customize the parameters of individual system so as to provide an enhanced model 264 of system behavior and improved accuracy of the mapping as described herein. The production SW tool can be used to determine customized LUTs of the system 2, and to provide enhanced calibration of system 2. The nominal values output from the generalized nominal system 242 at design execution stage can be output to the LUTs and software factors, which can be combined with the customized feedback 260 to provide an enhanced product. The modification to the LUTs to transform the system 2 from the generalized nominal system to the constructed system with customized parameters can be provided with calibration of the constructed system as described herein.

FIG. 5 shows a method 300 of calibration for laser system 2. The laser system 2 can be calibrated such that positions and angles of the components and actuators of the laser system are mapped onto locations of the eye 43. The method 300 can be performed on each build of a laser system, and can be used to improve the accuracy of a specific laser system. In many embodiments, the system specific calibration can be used to improve the correspondence between the treatment locations of the eye and the machine coordinates as described herein. Although reference is made to Z-axis alignment, similar methods and apparatus can be used to improve the accuracy of the system along other dimensions, such as X and Y dimensions, for example. Method 300 can be combined with optical breakdown threshold energy mapping as described herein, for example. Method 300 can be particularly well suited for calibration of the system with a first lens of the patient interface, in order to use a second lens of the patient interface to treat the patient accurately. A plurality of many additional patient interface lenses can be used based on the alignment with the first lens, for example. The methods and apparatus can be used to determine specific laser treatment parameters for a specific patient interface lens placed in the system for a specific eye, for example.

At a step 305, values of Xm, Ym, and ZL (where Xm corresponds to the angle of the X galvo mirror, Ym corresponds to the angle of the Y galvo mirror, and ZL corresponds to the movement of the lens in the Z-telescope) are determined within a treatment volume for the ultrafast femto second laser so as to provide corresponding X, Y and Z locations of the eye. The locations can be determined based on mapping and LUTs, for example. The mapped locations can depend on the location and shape of the optically transmissive structure such as lens 96, the distance 162, distance 164, and the distance 168, for example. The mapping locations may also depend on the laser characteristics such as beam quality, pulse width, polarization, and energy per pulse. The mapping locations may also depend on the characteristics of the optical system such as axial magnification, lateral magnification, numerical aperture, degree of telecentricity, aberration, and alignment.

At a step 310, values of Xm, Ym, ZL and ZED (where Xm, Ym, and ZL are defined as before and ZED corresponds to the position of the OCT reference path length stage) are determined within a measurement volume for the tomography system (such as the OCT system) so as to provide corresponding X, Y and Z locations of the eye or patient interface. The locations can be determined based on mapping and LUTs, for example. The tomography system may comprise one or more of an OCT system, a confocal system, a Scheimpflug system, an ultrasound system, or a high frequency ultrasound system, for example. The mapped locations can depend on the location and shape of the optically transmissive structure such as lens 96, the distance 162, distance 164, and the distance 168, for example. The mapping locations may also depend on the light source characteristics such as wavelength, spectral bandwidth, and polarization. The mapping locations may also depend on the characteristics of the optical system such as axial magnification, lateral magnification, numerical aperture, degree of telecentricity, aberration, and alignment.

At a step 315, values pixel X and pixel Y are determined within a measurement volume for the video system so as to provide corresponding X, Y, and Z locations of the eye or patient interface. The locations can be determined based on mapping and LUTs, for example. The video is primarily a two-dimensional mapping of Xm, Ym to X, Y. Because of the large depth of field of the imaging path and the telecentric form, the Z location remains unchanged for the range of Z for which the image is in focus. Accurate Z location can be determined using the OCT ranging system or a priori knowledge. The mapped locations can depend on the location and shape of the optically transmissive structure such as lens 96, the distance 162, distance 164, and the distance 168, for example. The mapping locations may depend on the characteristics of the optical system such as axial magnification, lateral magnification, numerical aperture, degree of telecentricity, aberration, and alignment.

At a step 320, a generic LUT is determined for the position parameters of the system in response to targeted locations of the eye. The generic LUT can combine the above mapped values of Xm, Ym, ZL, & ZED based on one or more of distance 162, distance 164, distance 168, dimension 152, dimension 154 or dimension 156, and combinations thereof for example. The generic LUT can be constructed based on ray tracing or other optically based analysis such as diffraction or wave based or gaussian beam propagation of the nominal optical components of the system and the movable components of the system to include the X galvo, the Y galvo, the Z-telescope, the attenuator, and the chair, for example. The generic values of the LUT can map each eye coordinate location to a specific location or angle of each of the values of Xm, Ym, ZL, & ZED and other machine controllable dimensions, for each of the UF laser, the OCT system and the video system and aim alignment, for example. Although a LUT is described, the mapping can be performed in one or more of many ways.

At a step 325, system specific corrections to the generic values are determined. The system specific LUT can be customized to the manufactured configuration of the system, and is capable of accommodating variation of the mapped components. The variation may occur with parts manufactured within specification but slightly different from the generic or nominal system. For example, the optical power, placement and dimensions of the manufactured components may differ slightly from the generic system. The system specific LUT can be generated based on the teachings described herein.

At a step 330, a system specific LUT(s) is determined based on the system specific corrections. The system specific LUT can be combined with the generic LUT in many ways, for example with corrections or adjustments comprising subtractions or additions and scalings to the generic LUT.

At a step 335, the system specific LUT is used to generate a laser treatment of the eye so as to form laser generated incisions of the eye. The system specific LUT can be combined with a treatment table comprising a plurality of eye coordinate references, so as to provide specific instructions to components of the laser system for each location of the eye treatment given variations in known dependencies such as from patient interface variations. The system specific LUT can be used to generate values of UF Xm, UF Ym, and UF ZL in order to control the positions of the corresponding components.

At a step 340, the system specific LUT is used to generate tomography values, such as values of OCT Xm, OCT Ym, OCT ZL and ZED values, so as to control Galvo Xm, Galvo Ym, Galvo Zm, and the OCT reference path length in order to image the eye and patient interface given variations in known dependencies such as from patient interface variations. The system specific LUT can be used to generate values of OCT Xm, OCT Ym, OCT ZL in order to control the positions of the corresponding components and ensure that the physical locations of the eye structures and patient interface are accurately mapped.

At a step 345, the system specific LUT is used to generate the Pixel X and Pixel Y values corresponding to the given X, Y, Z, and CL thickness and displacement values used to form an image of the eye and patient interface on the camera sensor array, and so as to accurately map the eye structures to three dimensional space in accordance with eye coordinate reference system 150.

Although the above steps show method 300 of calibrating in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 300 may be performed with the circuitry as described herein, for example one or more of the processor or logic circuitry such as the programmable array logic for field programmable gate array. The circuitry may be programmed to provide one or more of the steps of method 300, and the program may comprise program instructions stored on a computer readable memory or programmed steps of the logic circuitry such as the programmable array logic or the field programmable gate array, for example.

FIG. 6 shows an eye coordinate reference system 150 referenced to a lower surface of an optically transmissive structure as part of a patient interface. The optically transmissive structure may comprise a flat plate, or a lens having one or more curved surfaces. In many embodiments, the optically transmissive structure comprises lens 96. The objective lens 94 may comprise a plurality of achromatic infrared doubles, for example three achromatic infrared doublets. The reference location 180 may comprise the origin of the coordinate system 150, and can be located in one or more of many places, such as the posterior surface 96P of the optically transmissive structure, located opposite an anterior surface 96A of lens 96. The gap distance 168 between the cornea and posterior surface 96P can be within a range from about 1 to 10 mm, for example. The thickness 164 of the optically transmissive structure can be within a range from about 1 to 20 mm, for example about 12 mm. A distance 162 from the distal lower surface of the objective lens to the anterior surface 96A can be any suitable distance, for example within a range from about 10 mm to about 200 mm, for example about 20 mm. In many embodiments, the patient interface assembly comprises single use disposable structures to couple the optically transmissive structure comprising lens 96 to objective lens 94 and retention ring 97 of the patient interface assembly 14. The patient interface assembly may comprise a support structure 14S in order to place the optically transmissive structure to provide distance 162 and distance 168 in combination with thickness 164. The support structure 14S may comprise a stiff support so as to resist movement of the optically transmissive structure and patient ring 97 when the patient moves, for example. The support structure 14S may comprise an assembly of user combinable components such as retention ring 97, and a docking cone 14C, and an extension 14E, for example. The docking cone 14C can receive the lens 96 of the conic extension section 14E, for example.

Reference 180 location can be determined in one or more of many ways. In many embodiments, location 180 comprises an intersection of axis 99 with the posterior surface 96P of the optically transmissive structure as described herein. The location 180 may comprise a reference point determined with axis 99. For example a location 180 can be located along axis 99 that intersects the posterior surface 96P based on the measured system, and the location 180 may correspond to a distance of the posterior surface of the specific system lens as compared to the lower surface of the generalized system. Alternatively, the location 180 may comprise a distance from an internal structure of laser system 2 such as a mirror of the OCT system, or a distance from the surface of one of the objective lenses such as the posterior surface of the achromatic objective lens closest to the eye. The location of axis 99 can be determined based on system calibration, and the calibration may comprise determining a location of axis 99 that retro reflects the laser beam to a point of origin within system 2, for example. The axis 99 may comprise the origin of the patient reference system 150, for example.

The deviation of the lower surface of a constructed system from the location of the generalized system can be determined and the values of the LUT determined accordingly.

The lens 96 may comprise a convexly curved posterior surface so as to urge gas bubbles to the periphery and away from the optical beam path when the posterior surface 96P contacts a liquid interface fluid, such one or more of water, saline, viscous fluid, or a viscoelastic fluid. The anterior surface 96A can be provided with a curved shape or a flat shape, for example. In many embodiments, the convexly curved lower surface can extend the working range of the laser system so as to provide optical breakdown over an increased range within the eye, for example with combined corneal and cataract surgery. The dimensions of lens 96 can be determined so as to provide the extended range when spaced apart from the cornea and combined with one or more doublet lenses by a person of ordinary skill in the art based on the teachings described herein. The negative lens of the Z-telescope optics may comprise radii of curvature to provide the extended range of optical breakdown when combined with the lens 96 and the one or more achromatic objective lenses. The aberrations can be controlled over the intended imaging and cutting volume of the eye and patient interface due to the balancing of contributions from the Z-telescope, the objective, and the contact lens as a function of positions of the Z-telescope, the X & Y galvos, and the variation of placement and thickness of the contact lens by a person of ordinary skill in the art of lens design.

The lens 96 can be configured to provide a different change in the numerical aperture of the beam focus than a flat plate, for example. In many embodiments, the lens 96 contributes a relatively small amount of focusing power when the laser beam is scanned near the cornea. However, when the laser beam is scanned at locations deeper in the eye, for example near the lens capsule, the lens 96 can provide a greater affect on the beam focus than when the beam is focused near the cornea, so as to further change the numerical aperture of the laser beam, for example.

FIG. 7A shows a look up table 210 for an UF laser as described herein. The LUT 210 may comprise a plurality of discrete input values 212 over a range, for example four values such as X, Y, Z of patient coordinate reference system and distance CL of the lower surface of the lens, and a plurality of output values 214. The X and Y values of the eye can range from −8 to 8 mm, in 0.25 mm increments, for example. The Z value can range from 0 to 17 mm in 0.25 mm increments, for example. The CL value can range from −1 to 1 mm in 0.5 mm increments, for example. These four dimensional input values can be input into processor system and an output machine value provide for each combined input. The output values 214 of the look up table can be provided as Xm, Ym and ZL for each combined input value combination. The output of Xm and Ym can each be within a range from −8.59 degrees to 8.59 degrees of the corresponding galvanometer mirror. The output value for ZL can be within a range from 3.7 to 20.7 mm, for example. The total number of input and values of the LUT can be about 1,457,625 for each input comprising (X, Y, Z, CL) and each output comprising (Xm, Ym, ZL), for example.

FIG. 7A1 shows an optical schematic of the components corresponding to the LUT of FIG. 7A. The optical schematic shows the components as described herein used to determine the LUT for the UF pulsed laser 64, for example with reference to FIG. 4A. The laser beam 66 can be transmitted through zoom optics 68 to a limiting aperture to determine beam size 72. The limited beam proceeds to relay lenses 80 and then to the optical Z-telescope lenses 84. The distance ZL is varied, and ZL can be programmed into optical modeling software as described herein. The beam 66 is then transmitted to X and Y galvos 86, 88 to deflect the beam passed to the objective lenses 94 (hereinafter "OBJ"). The objective lens 94 focuses the laser beam 66 toward the optically transmissive structure, which may comprise a plate or lens 96 as described herein, for example. The distance from the objective lens 94 to the optically transmissive structure CLopt can be used to determine the location of the optical breakdown, and the thickness of the optically transmissive structure (hereinafter "CLth") can be used to determine the location of optical breakdown.

FIG. 7A2 shows input and output of the LUT as in FIGS. 7A and 7A1. The input parameters are the X, Y and Z locations of the optical breakdown within the mapped treatment volume, the distance from the objective lens to the anterior surface of the optically transmissive structure, and the thickness of the optically transmissive structure of the patient interface. The output of the LUT comprises the X mirror position for the UF laser (hereinafter "Xm(UF)"), the Y mirror position for the UF laser (hereinafter "Ym(UF)"), and the position of the Z-telescope lens (hereinafter "ZL (UF)")

FIG. 7A3 shows structure of the LUT via an excerpt of the LUT as in FIGS. 7A and 7A1. The LUT comprises a header 270, a body 271, and columns 272 corresponding to the mapped coordinates of the system as described herein. Although a low resolution is shown the table may comprise a high resolution table readily constructed by a person of ordinary skill in the art based on the teachings described herein.

The header 270 may comprise a description of the table and laser system components, for example. The header 270 may comprise the input and output parameters such as the output parameters Xm(UF) in degrees, Ym(UF) in degrees, ZL(UF) in mm, for the UF laser wavelength, and the header 270 may comprise the input parameters such as the X, Y and Z coordinates of treatment in the eye in millimeters, the thickness of the optically transmissive structure CLth, and the position of the posterior surface of the optically transmissive structure CLopt, The header 270 may comprise baseline expected locations and coordinate references of identifiable structures, such as reference locations of the origin of the coordinate reference system, the location of the cornea along the Z axis, the location of the limbus along the X axis and the location of the limbus along the Y axis. The mapped positions of the system components can be provided for each of these input locations, such as the X and Y mirror positions, Xm(UF), Ym(UF). Also included in the header 270 are the Z-telescope position ZL(UF), The ZED(UF) position as shown in the figures, the delta Z value (hereinafter "Dz") which may comprise a correction, and the Strehl ratio which can be used to determine the quality of beam focus and adjustment to the location of optical breakdown. One of the purposes of the header 270 is to provide a sample of key points within the look up table. These key points may be compared to multiple executions of the model to generate the look up table. These key points can be used as watch points to gain an overview of the performance of the model run and can be used to determine the health or veracity of the look up table.

The Dz can be determined in one or more of many ways, and can be determined based on the computer modeling as described herein. Alternatively or in combination, the value of Dz can be determine based on measurements of a constructed system as described herein, for example.

The body 271 of the LUT may contain the values of the LUT. The values can be determined based on optical modeling as described herein. Each value of the table may comprise a Step comprising a location of the record of the table, ZL, X, Y and Z coordinates, CLopt, CLth, Xm(UF), Ym (UF), ZL (UF), a value Dz at the location, the Strehl ratio, and a flag. The flag may be indicative of the stability of the model run in generating the look up table. Dz for example can be used as a metric as to whether the model adequately converges to a solution. In general, the generic LUT is automatically generated using an optical program using a merit function and a set of variables to reduce a custom designed error function. Dz is then calculated by the program using a different mode or definition of best focus. Ideally these would arrive at the same solution but as the beam becomes more aberrated as a function of position these two methods may differ as expressed in Dz. The flag can then be toggled to a set the value of Dz. For example, the flag may equal 1 when the Dz is with 10 um or 0.010 in the table of FIG. 7A3 and set to 0 when outside this value. In this way, the automatic reading by system software of the LUT can using this value as an indication of the acceptable cut zone.

FIG. 7B shows a LUT 220 for an OCT system. The look up table 220 may comprise a plurality of discrete input values 222 over a range, for example four values such as X, Y, Z of patient coordinate reference system and distance CL of the lower surface of the lens, and a plurality of discrete output values 224. The X and Y values of the eye can range from −8 to 8 mm, in 0.25 mm increments, for example. The Z value can range from 0 to 17 mm in 0.25 mm increments, for example. The CL value can range from −1 to 1 mm in 0.5 mm increments, for example. These four dimensional input values can be input into processor system and an output machine value provide for each combined input. The output values 224 of the look up table can be provided as Xm, Ym and ZL for each combined input value combination. The output of Xm and Ym can each be within a range from −8.59 degrees to 8.59 degrees of the corresponding galvanometer mirror. The output value for ZL can be within a range from 3.7 to 20.7 mm, for example. The output value of ZED of the OCT aim can be provided based on the teaching described herein. The output value ZED can be configured to provide adjustment to the OCT arm over the full range of motion of the Z-telescope moving lens in order to provide coherence to the OCT system, for example. The total number of input of the LUT can be about 1,457,625 for each input comprising (X, Y, Z, CL) and each output comprising (Xm, Ym, ZL, ZED), for example. The output and input mapping process can be switched. The OCT ranging system is a measurement device used to find intended surfaces. In this way, the values of OCT Xm, OCT Ym, OCT Zl, and ZED are determined once the targeted surface is located. These are used as input values to generate output values for X, Y, and Z for the location of the intended targeted structure. These output values for X, Y, Z along with measured values for CL can then be used as input to the UF LUT 212 to determine the output UF Xm, UF Ym, UF ZL for placing cuts.

FIG. 7B1 shows an optical schematic of the components corresponding to the look up table of FIG. 7B. The optical schematic shows the components as described herein used to determine the LUT for the OCT system, for example with reference to FIG. 4A. The measurement beam can be transmitted to a reference arm with a beam splitter 100. The portion of the beam 102 transmitted through the beam splitter 100 is transmitted to the optical Z-telescope lenses 84. The distance ZL is varied, and ZL can be programmed into optical modeling software as described herein. The beam 102 is then transmitted to X and Y galvos 86, 88 to deflect the beam 102 passed to the objective lenses OBJ 94. The objective lens 94 focuses the laser beam 102 toward the optically transmissive structure, which may comprise a plate or lens 96 as described herein, for example. The distance from the objective lens to the optically transmissive structure CLopt can be used to determine the location of the measurement location corresponding to optical breakdown, and the thickness of the optically transmissive structure CLth can be used similarly.

The OCT measurement may comprise an optical path length hereinafter (OPL) that can be referenced from one or more of many locations of the OCT measurement system, such as the output aperture from the light source of the OCT measurement beam.

FIG. 7B2 shows input and output of the LUT as in FIGS. 7B and 7B1. The input parameters are the Xm, Ym and ZL locations of the OCT measurement beam within the mapped treatment volume, the distance from the objective lens to the anterior surface of the optically transmissive structure CLopt, the thickness of the optically transmissive structure of the patient interface, CLth, and the location of measurement arm ZED(OCT). The output of the LUT comprises the X position for the OCT measurement beam (hereinafter "X(OCT)"), the Y position for the OCT measurement beam (hereinafter "Y(OCT)"), and the Z position (hereinafter "Z(OCT)") for the OCT measurement beam.

FIG. 7B3 shows structure of the LUT as in FIGS. 7B and 7B 1. The LUT comprises a header 273, a body 274, and columns 275 corresponding to the mapped coordinates of the system as described herein. Although a low resolution is shown the table may comprise a high resolution table readily constructed by a person of ordinary skill in the art based on the teachings described herein.

The header 273 may comprise a description of the table and laser system components, for example. The header 273 may comprise parameters such as Xm(OCT) in degrees, Ym(OCT) in degrees, ZL(OCT) in mm, for the OCT laser wavelength, and the header 273 may comprise the parameters such as the X, Y and Z coordinates of the measurement beam in the eye in millimeters, the thickness of the optically transmissive structure CLth, and the position of the posterior surface of the optically transmissive structure CLopt from the posterior surface of the objective lens. One of the purposes of the header 273 is to provide a sample of key points within the LUT. These key points may be compared to multiple executions of the model to generate the LUT. These key points can be used as watch points to gain an overview of the performance of the model run and can be used to determine the health or veracity of the LUT.

The header 273 may comprise baseline locations and coordinate references of identifiable structures, such as reference locations of the origin of the coordinate reference system, the location of the cornea along the Z axis, the location of the limbus along the X axis and the location of the limbus along the Y axis. The mapped positions of the system components can be provided for each of these locations, such as the X and Y mirror positions, Xm(OCT), Ym(OCT). Also included in the header are the z-telescope position ZL(OCT), the ZED(OCT) position as shown in the figures, the delta Z value (hereinafter "Dz") which may comprise a correction, and the Strehl ratio which can be used to determine the quality of measurement beam focus.

The OCT Dz can be determined in one or more of many ways, and can be determined based on the computer modeling as described herein. Alternatively or in combination, the value of Dz can be determine based on measurements of a constructed system as described herein, for example. The value of the OCT Dz may comprise a map from the measured OCT location to the optical breakdown location, for example.

The body 274 of the LUT may contain the values of the LUT. The values can be determined based on optical modeling as described herein. Each value of the table may comprise a step comprising a location of the record of the table, ZL, X, Y and Z coordinate, CLopt, CLth, Xm(OCT), Ym (OCT), ZL (OCT), a value Dz at the location, the Strehl ratio, and a flag. The flag may be indicative of the stability of the model run in generating the look up table. Dz for example can be used as a metric as to whether the model adequately converges to a solution. In general, the generic LUT is automatically generated using a optical program using a merit function and a set of variables to reduce a custom designed error function. Dz is then calculated by the program using a different mode or definition of best focus. Ideally these would arrive at the same solution but as the beam becomes more aberrated as a function of position these two methods may differ as expressed in Dz. A flag can then be toggled to a set the value of Dz. For example, the flag may equal 1 when the Dz is with 10 um or 0.010 in the table of FIG. 7B3 and set to 0 when outside this value. In this way, the automatic reading by system software of the LUT can using this value as an indication of the acceptable cut zone.

FIG. 7C shows a LUT 230 for a video camera. The LUT 230 may comprise a plurality of discrete input values 232 over a range, for example four values such as X, Y, Z of patient coordinate reference system and distance CL of the lower surface of the lens, and a plurality of discrete output values 234. The X and Y values of the eye can range from −9 to 9 mm, in 1 mm increments, for example. The Z value can range from 6 to 10 mm in 1 mm increments, for example. The CL value can range from −1 to 1 mm in 0.5 mm increments, for example. These four dimensional input values can be input into processor system and an output machine value provide for each combined input. The output values 234 of the LUT can be provided as Pixel X, Pixel Y, and the range of Pixel X and Pixel Y can each be from about −543 pixels to about 543 pixels. The output and input mapping process can be switched. The video system is a measurement device used to find intended surfaces. The video system is also used as target aid for the user to place cuts. In these ways, the values of Pixel X and Pixel Y are determined using the video image. The values of Pixel X and Pixel Y along with either assumptions or measurements made for Z and CL are used as input values to generate output values for X, Y, and Z for the location of the intended targeted structure. The output values for X, Y, Z along with measured values for CL can then be used as input to the UF LUT 212 to determine the output UF Xm, UF Ym, UF ZL for placing cuts.

The LUT 210, the LUT 220, and the LUT 230 can be combined in one or more of many ways to treat the patient. Further, inverse LUTs can be determined so as to map from machine parameters to parameter of the eye. In many embodiments, the OCT LUT 220 is used to image the eye and patient interface with OCT at a series of discrete OCT locations based on commands to the laser system to in order to scan a target region of the eye. The scan data for the locations of the eye can then be input into the LUT 210 for treatment table generation and planning, and the patient treated with the output 214 from treatment table 210.

The data for each LUT can be interpolated, for example with known interpolation methods. For example, the interpolation may comprise linear interpolation based on values of closest neighbors provided to the look up table. The LUT can be extrapolated to extend the ranges.

The LUTs as described herein are provided in accordance with examples, and a person of ordinary skill in the art will recognize many alternatives and variations.

FIG. 7C1 shows an optical schematic of the components corresponding to the LUT of FIG. 7C. The optical system forms an image on the camera array 276 comprising x pixels at x pixel locations (hereinafter "Pix X") and y pixels at y pixel locations (hereinafter Pix Y). The image is formed with a plurality of fixed focus lenses 278. The image beam 282 passes through an aperture stop 280 located between the fixed focus lenses 278 to arrive at the sensor array 276. A field stop 284 is provided along with another fixed focus lens 286 optically coupled to the objective lenses 94. The patient interface and distances are described herein.

FIG. 7C2 shows input and output of the LUT as in FIGS. 7C and 7C1. The input comprises the measured Pix X and Pix Y coordinate references of the CCD array. The input may also comprise the Z focus location of the eye, and the CLopt and CLth parameters. The output comprises the X and Y coordinate references of the eye at the input Z depth.

FIG. 7C3 shows the structure of the LUT as in FIGS. 7C to 7C2. Although a low resolution table is shown, the high resolution table can readily be constructed by a person of ordinary skill in the art based on the teachings described herein. The structure of the table comprises a header 287 and a body 288 comprising columns 289 of the table.

The header 287 may comprise the input and output parameters for the wavelength of the video imaging system. The parameters may comprise the X, Y and Z locations of the imaging system within the eye and the parameters may comprise the corresponding X pixels (Pix X) and Y pixels (Pix Y). The header 287 may comprise coordinate reference locations corresponding to tissue structures of the eye, such as the iris or the limbus, for example. The coordinate reference locations may comprise a location within the eye along the axis of the system at coordinates X=0, Y=0 and Z=8 mm, for example. The corresponding mapped X and Y pixel coordinates for X=5 mm and Y=5 mm can be provided at pixel coordinate locations of approximately 303 pixels, respectively, for example. One of the purposes of the header 287 is to provide a sample of key points within the LUT. These key points may be compared to multiple executions of the model to generate the LUT. These key points can be used as watch points to gain an overview of the performance of the model run and can be used to determine the health or veracity of the LUT.

Figure 8:
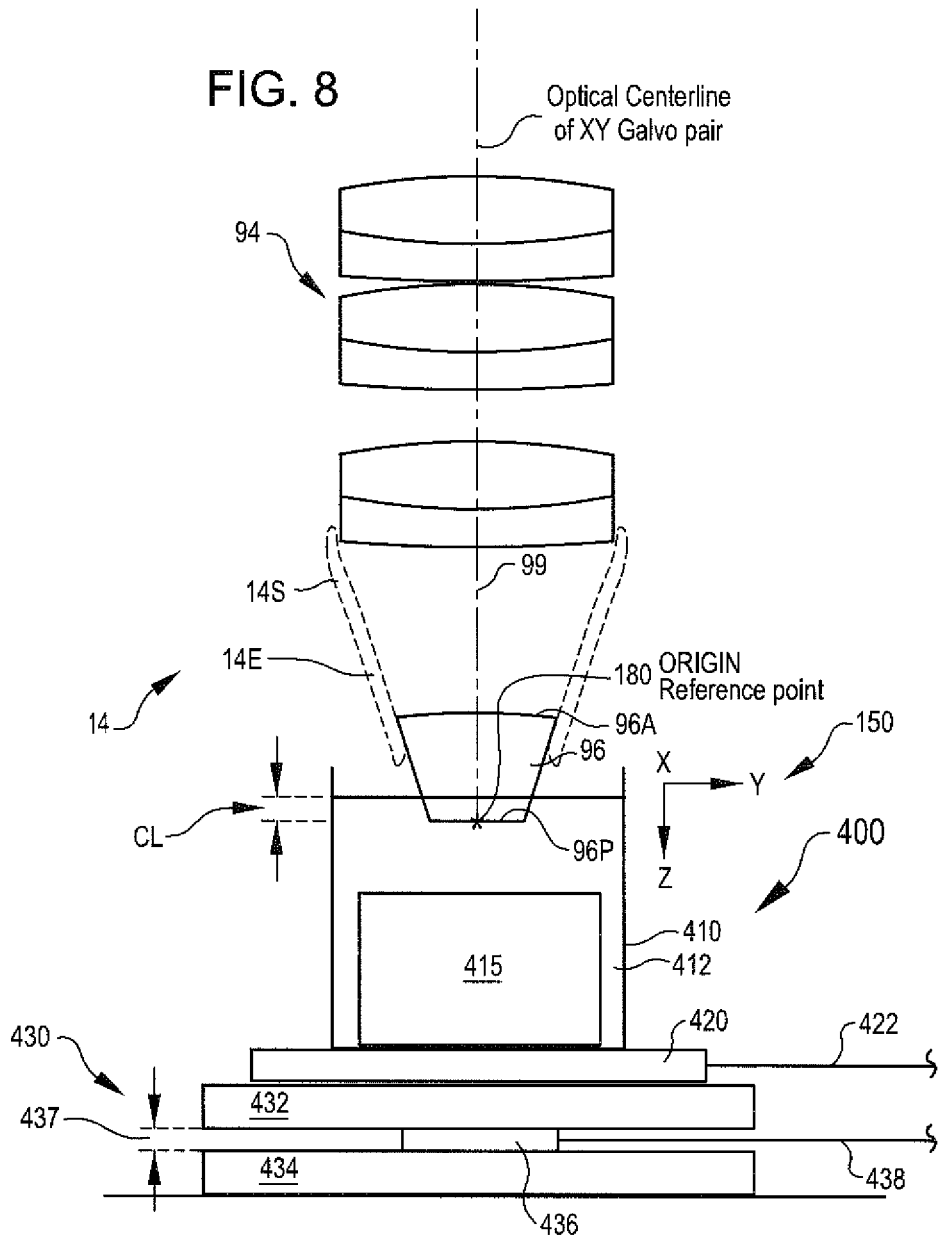
FIG. 8 shows a calibration apparatus to measure and map optical breakdown locations along the laser beam path, in accordance with many embodiments.

The body 288 of the LUT may comprise the Pixel X, Pixel Y, Z, CLopt, Clth, input parameters. The output of the LUT may comprise the output X and Y locations for each input record, for example. The corresponding diameter of the spot can be provided at each location in pixels, and a logic flag can be provided for each location. The logic flag may comprise one or more of many logic signals, and may correspond to whether the image of tissue is to be provided at the location, or whether the focus of the treatment beam at the mapped X Pix and Y Pix location is suitable for treatment, for example, FIG. 8 shows a calibration apparatus 400 to measure and map optical breakdown locations along the UF laser beam path of system 2. The measured optical breakdown can be performed at the factory prior to shipping the laser system, or in the field, or combinations thereof, for example. The apparatus 400 may comprise components of patient interface assembly 14, a container 410, a beam blacker 415, a transducer to measure optical breakdown such as hydrophone 420, and a translation stage 430. The patient interface assembly 14 and a can be used to measure the optical breakdown along the laser beam path, and may comprise the support 14S coupled to the extension 14E so as to place the optically transmissive structure which may comprise lens 96 at a location along axis 99. In many embodiments, the reference location 180 can be established based on measurements of posterior surface with the tomography system such as the OCT system as described herein. The OCT system can be previously calibrated so that the ranging numbers are accurate and are used for this calibration. An example of prior OCT calibration includes a set of mechanically referenced distances in water and glass. These standards are used to find the optical path length as a function of X, Y, & Z. These standards can be a set of tools at set distances, reticles with calibrated scales, materials of known thicknesses, and material of known refractive index. The measurement of known distances and positions can be used to find the group index for each material. This group index and therefore calibrated ranging are then used as part of this calibration procedure to determine accurate X, Y, Z positions. The distance CL can be established as part of this calibration process, and the LUTs determined based at least in part on the measured value of CL for the text apparatus.

The container 410 may comprise any suitable container such as a beaker. The container may contain a suitable liquid to model optical breakdown within the eye, such as water, saline, a viscous material, or a viscoelastic material, for example. The material may have the phase group index known in a previous calibration step so that the OCT ranging system may be used to detect the absolute location of the immersed surfaces. The beam block 415 comprises a beam absorbing material, for example. The laser beam focused below the surface of the beam block cannot provide optical breakdown in many embodiments. As the beam block is lowered, the optical breakdown can be detected with the transducer which may comprise hydrophone 420. A person of ordinary skill in the art will recognize that the transducer may comprise one or more of many suitable transducers such as a hydrophone, a microphone, a piezoelectric transducer, and one or more of many known transducers, for example.

The translation stage 430 may comprise a manual or automated translation stage with a micrometer 436 so as to accurately measure the position and change of position of the upper surface of the block 415. The translation stage 430 may comprise an upper platform 432, a lower platform 434 with portion of micrometer 436 coupled in between.

The calibration of the optical breakdown depth can be performed in many ways and can be performed at various energy levels. In some embodiments, the optical breakdown depth calibration can be performed after the energy threshold mapping so that the energy used to calibrate the depth of the optical breakdown can be tailored for the location, for example.

The optical breakdown energy can be determined by setting the laser beam output to a desired energy level, for example with adjustment to the attenuator. The upper surface of the optical block can be raised to a position above the target location. The laser can be scanned along a target plane or other surface corresponding to the upper surface of the optical block, and optical breakdown event measured with the hydrophone 420. The optical surface distance and topology may be measured by the OCT system. The optical block can be lowered a useful amount, for example 5 um. The scan along the plane can be performed again and the location of optical breakdown events determined, and in many embodiments the scan may not fire the laser at locations that have previously received optical breakdown to facilitate evaluation of the measurement data. The optical block can be lowered further and additional scans repeated until the depth optical breakdown as a function of depth has been measured for each location of the scan pattern. The scan pattern may comprise one or more of many shapes, and may comprise a grid, for example.

The optical breakdown for the individual laser system can be measured at a plurality of depths and transverse locations. In many embodiments, the location of optical breakdown along the laser beam path can be measured with plurality of planes and a grid pattern distributed substantially along each plane so as to define an error surface for each plane. For example, depths of the UF LUT adjustment can be determined using the calibrated OCT system at each of 5, 6.5, 8, 9.5, 11, and 12.5 mm from the reference location, for example. For the first three depths corresponding to corneal locations, more data can be measured than the last three depths corresponding to locations posterior to the cornea, for example.

The input may comprise the three dimensional location of a laser beam pulse and the output may comprise the error from the expected target depth for the location of the laser beam pulse, which can be used to adjust the machine coordinate reference to provide optical breakdown at the correct depth.

Figure 9A:
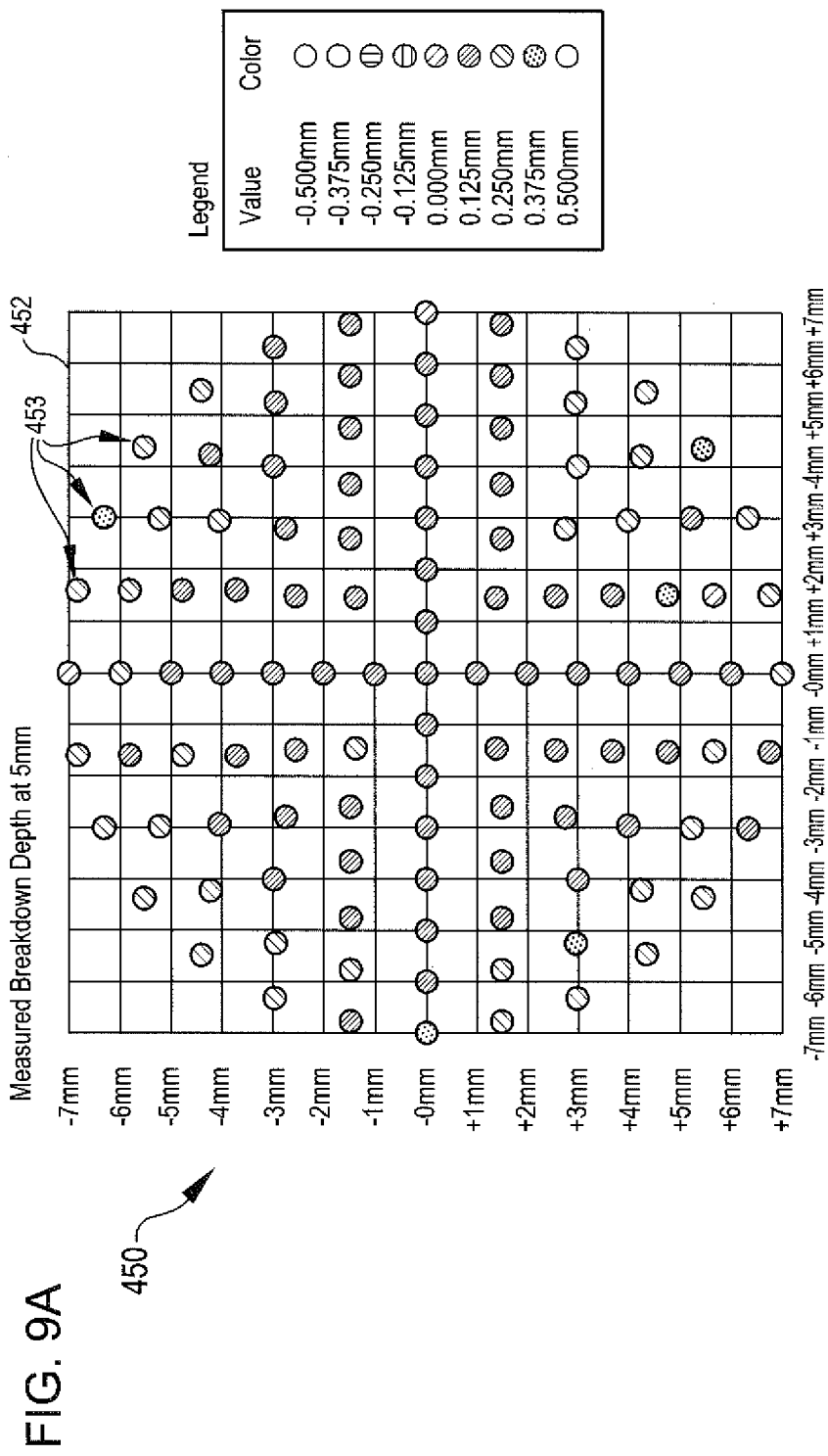
FIG. 9A shows a map of deviation in depth from the expected plane as measured by optical breakdown at a plurality of locations of the optical beam path corresponding to a plane near a vertex of a cornea, in accordance with many embodiments.

FIG. 9A shows a 450 map of a plurality of optical breakdown locations 453 along the optical beam path deviating from a target or expected depth 452 corresponding to a plane near a vertex of a cornea. The plane can be located at a distance of 5 mm from the reference location 180 along axis 99, for example. The plane distance may be measured using the previously calibrated OCT ranging system. The depths of the measured optical breakdown can deviate from the target depth of 5 mm by an amount shown in the legend. Although many of the values are within a range from about +0.125 mm to about −0.125 mm, the accuracy of the system can be further improved with the adjustment to the target location as described herein.

Figure 9B:
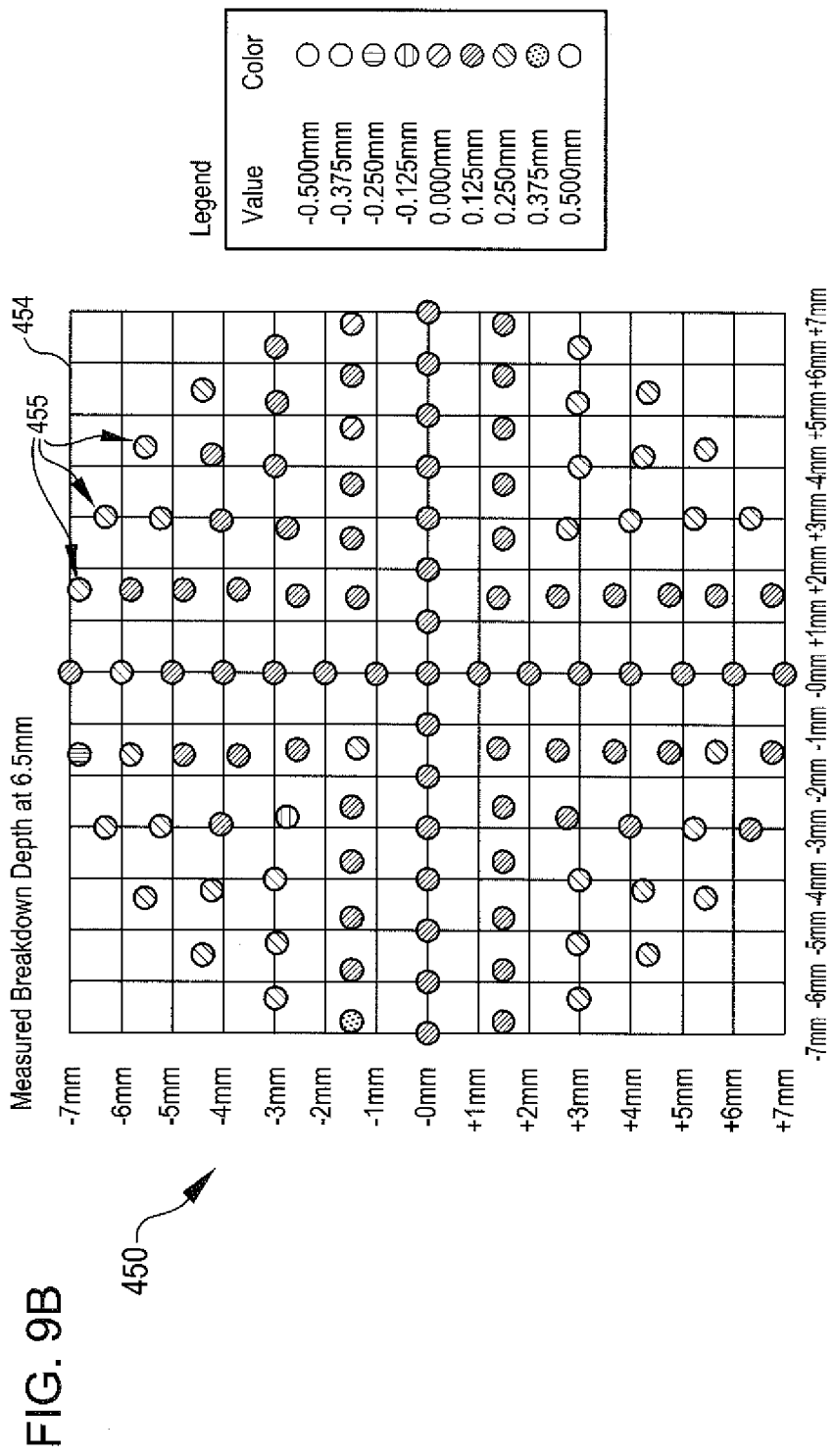
FIG. 9B shows a map of deviation in depth from the expected plane as measured by of optical breakdown at a plurality of locations of the optical beam corresponding to a plane intersecting a cornea between a vertex of the cornea and an limbus of the eye, in accordance with many embodiments.

FIG. 9B shows map 450 of a plurality of optical breakdown locations 455 along the optical beam path deviating from a target depth 454 corresponding to a plane intersecting a cornea between a vertex of the cornea and the limbus of the eye. The limbus of the eye may comprise tissue near the intersection of the cornea and the sclera. The plane can be located at a distance of 6.5 mm from the reference location 180 along axis 99, for example. The depths of the measured optical breakdown can deviate from the target depth of 6.5 mm by an amount shown in the legend. Although many of the values are within a range from about +0.125 mm to about −0.125 mm, the accuracy of the system can be further improved with the adjustment to the target location as described herein.

Figures 9C, 9D:
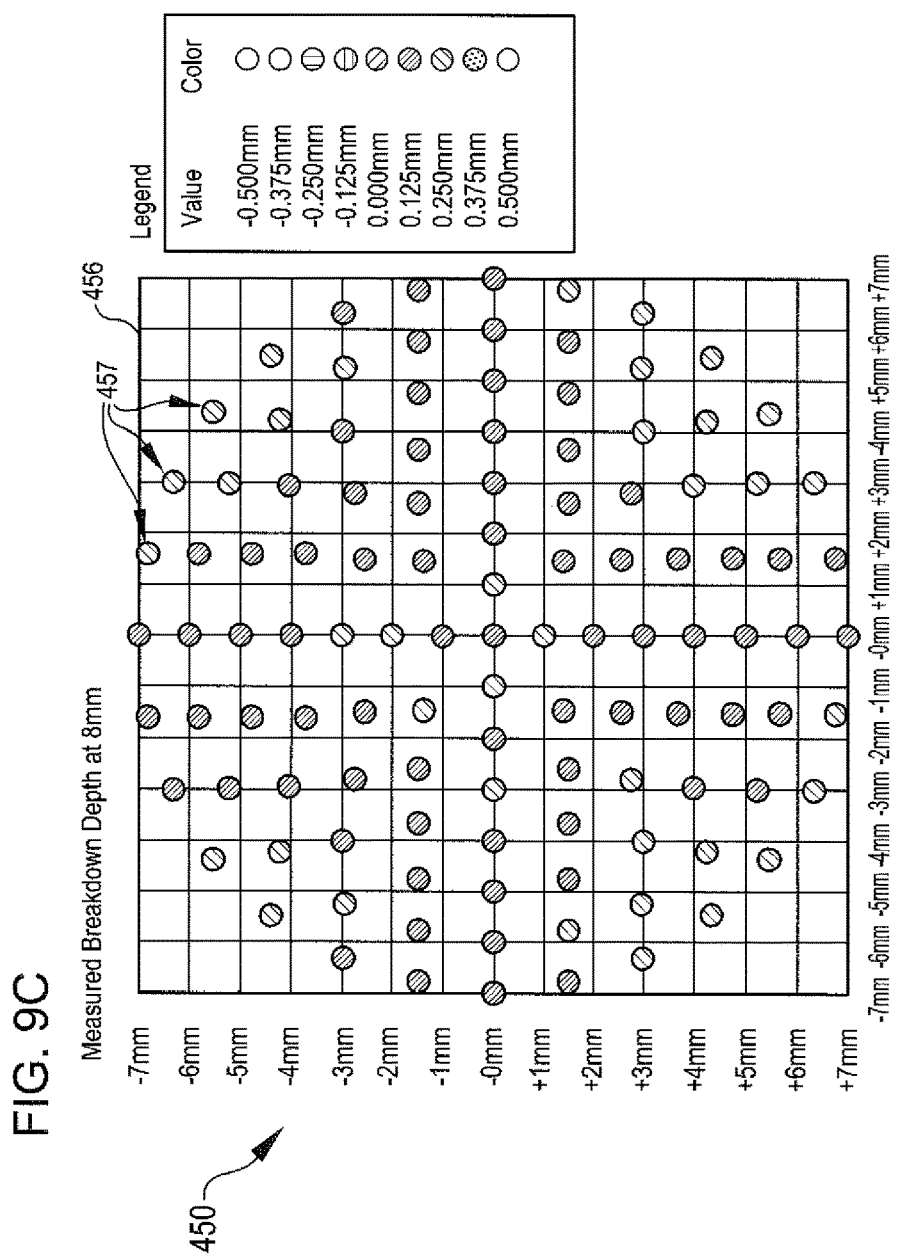
FIG. 9C shows a map of deviation in depth from the expected plane as measured by optical breakdown at a plurality of locations of the optical beam corresponding to a plane intersecting a peripheral portion of the cornea located near the limbus of the eye, in accordance with many embodiments.
FIG. 9D shows error coefficients to be applied as calibration corresponding to depth errors over a treatment volume based on the measurements of FIGS. 9A to 9C, in accordance with many embodiments.

FIG. 9C shows map 450 of optical breakdown at a plurality of locations 457 along the optical beam path deviating from a target depth 456 corresponding to a plane intersecting a peripheral portion of the cornea located near the limbus of the eye. The plane can be located at a distance of 8 mm from the reference location 180 along axis 99, for example. The depths of the measured optical breakdown can deviate from the target depth of 8 mm by an amount shown in the legend. Many of the values are within a range from about +0.125 mm to about 0.25 mm and the accuracy of the system can be further improved with the adjustment to the target location as described herein.

FIG. 9D shows error coefficients corresponding to depth errors over a treatment volume based on the measurements of FIGS. 9A to 9C, and may comprise additional measurements at additional depths corresponding to treatment as described herein, for example. The error at a target location comprising patient coordinate references of dimension 152, dimension 154 and dimension 156, for example X, Y, and Z, can be expressed as a function of X, Y, and Z denoted as F(X,Y,Z). The function F(X,Y,Z) may provide an amount of Z axis error of the optical breakdown along the dimension 156 corresponding to the dimension of the laser beam path, for example. The shown coefficients are for a polynomial of the form:

$$F(X,Y,Z)=C0+C1*X+C2*Y+C3*Z+C4*X^2+C5*Y^2+C6*X*Y$$

Where '*' indicates multiplication and '^' denotes exponential power such as a square. The polynomial may comprise one or more of many known polynomials such as Taylor or Zernike polynomials for example. In many embodiments the polynomials can be used to generate lookup tables, for example.

The function can include additional input, such as the distance CL of the location 180 from the target plane, the thickness of the lens 86, the energy of the laser and can be a four, five, or other dimensional input, for example. An example input to the Z axis error function F(X,Y,Z,E) can be X, Y, Z and E, where E is the energy of the laser, which can be adjusted in many ways for the treatment, for example with the attenuator. An example input to the Z axis error function F(X,Y,Z, CL) can be X, Y, Z and CL, where CL is the measured distance of the posterior surface of the optically transmissive structure such as the plate or lens 96, for example. The input may comprise the thickness of the optically transmissive structure CLTH, for example. In many embodiments, the input to the Z axis error may comprise a 6 dimensional input X, Y, Z, E, CL and CLTH to a function F(X, Y, Z, E, CL, CLTH), which provides an output error of the optical breakdown along Z axis dimension 156, for example.

Figures 10A, 10B:
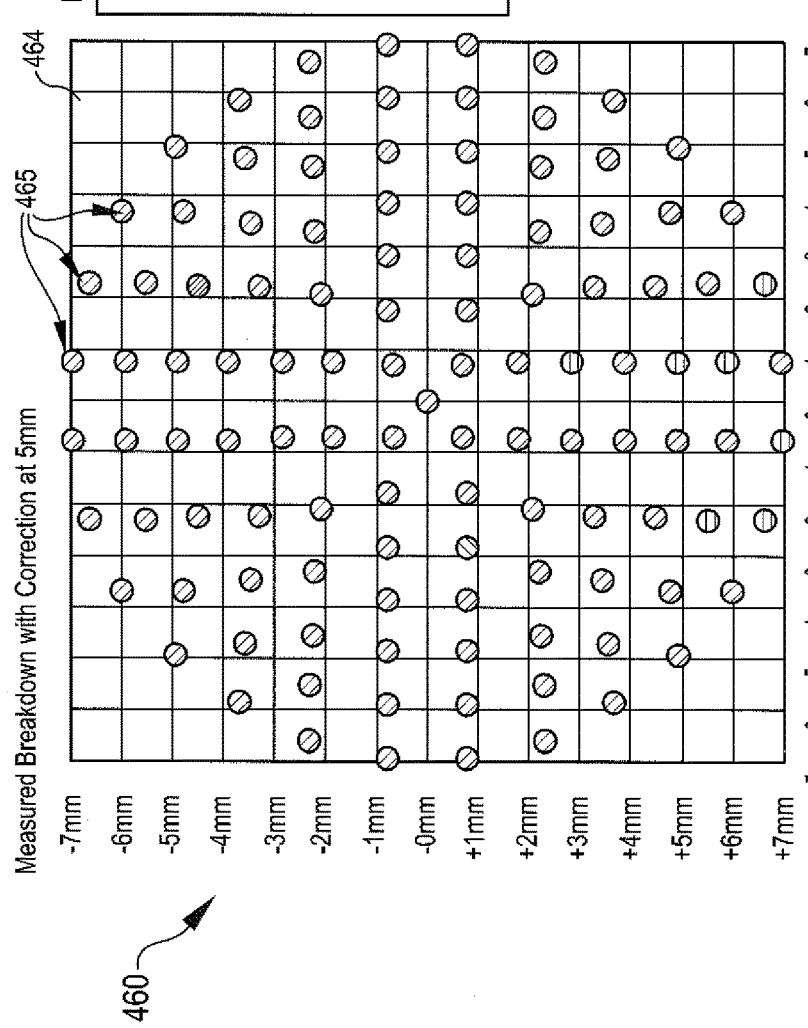
FIG. 10A shows verification of the correction or calibration based on correction of the error coefficients as in FIG. 9D, in accordance with many embodiments.
FIG. 10B shows error coefficients corresponding to depth corrections over a treatment volume, in accordance with many embodiments.

FIG. 10A shows verification of the correction based on correction of the error coefficients as in FIG. 9D. The map 460 of optical breakdown locations for the plurality of measurements 460 along the depth 464 of 5 mm is shown. The laser system has been updated with LUTs to correct the values of the Z axis optical breakdown. The measurements can be repeated at each of the measurement plans, for example at 5, 6.5, 8, 9.5, 11, and 12.5 mm measurement planes and the errors fit to the polynomial. This measured result shows a significant improvement in accuracy, and many of the measured values are within the range from +0.125 to −0.125 over a much greater region of the measurement area.

FIG. 10B shows error coefficients corresponding to depth corrections over a treatment volume comprising the depth shown in FIG. 10A and the additional measurement depths along planes. The coefficients are much smaller, showing that the depth correction has worked.

Figure 11:
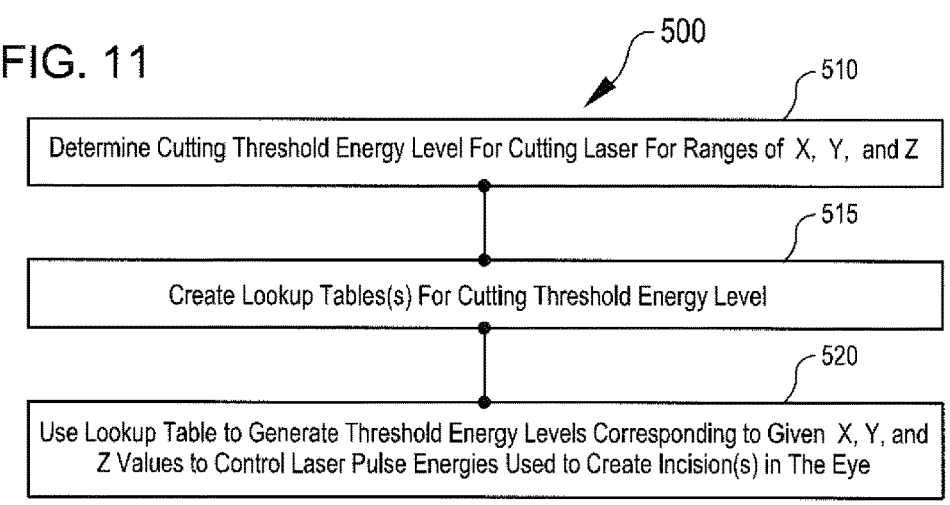
FIG. 11 shows a method of cutting tissue in response to threshold energy mapping, in accordance with many embodiments.

FIG. 11 shows a method 500 of cutting tissue in response to threshold energy mapping as described herein.

At a step 510, optical breakdown energy cutting thresholds are determined for laser ranges in a plurality of dimensions as described herein, and the threshold energy can be mapped to a plurality of dimensions comprising the X, Y and Z dimensions, for example. The optical breakdown threshold energies can be combined with the system specific Z-axis calibration as described herein, for example. The energy threshold mapping can be determined with ray tracing or other optical modeling for a general system and used for many systems. Alternatively or in combination, the optical breakdown threshold energy mapping can be system specific.

At a step 515, LUTs are generated for the cutting threshold levels at each location, and can include additional laser parameters and patient interface parameters as described herein. The LUTs can be determined based on the mapping of the threshold amounts of energy as described herein.

At a step 520, the LUT is used to generate the laser energy treatment amounts corresponding to the given X, Y, and Z values of the treatment, and additional values. The cutting threshold levels can be used to determine the laser energy at each location, and the treatment energy can be increased above the threshold level at each location so as to provide cutting with a safety margin above the threshold level. The cutting margin may comprise an amount, or a ratio such as a percentage above the threshold amount. For example, the threshold margin may comprise a 1 uJ increase in the pulse energy from the laser added to the mapped amount. Alternatively or in combination, the threshold margin may comprise a multiplier, for example a 1.5× multiplier that increases the amount of energy by 50% at a location based on the threshold energy at the pulse location. The LUTs as described herein can be used to readily determine the threshold amount of energy at a location, and the look up tables can be calculated so as to comprise the amount above threshold. Alternatively or in combination, the increase above the mapped threshold energy can be provided on a location by location basis.

The laser is pulsed with the energy adjusted in response to the mapped energy. The laser scan pattern can be configured to treat neighboring areas having similar amounts of energy, for example. Alternatively, the laser attenuator may comprise a fast laser attenuator, such as a galvanometer mounted attenuator, a prismatic attenuator, or an electronic switch, such that the laser pulse energy can be adjusted dynamically across a scan of the eye, for example a scan along a direction with the X or Y galvo. A person of ordinary skill in the art will recognize many adaptations and variations of the scan pattern based on the teachings described herein so as to provide rapid scanning with rapid energy changes to the laser beam pulses in response to the mapped energy.

Although the above steps show method 500 of cutting tissue in response to threshold energy mapping in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as is beneficial to the treatment.

One or more of the steps of the method 500 may be performed with the circuitry as described herein, for example one or more of the processor or logic circuitry such as the programmable array logic for field programmable gate array. The circuitry may be programmed to provide one or more of the steps of method 500, and the program may comprise program instructions stored on a computer readable memory or programmed steps of the logic circuitry such as the programmable array logic or the field programmable gate array, for example.

Other apparatus may be used to attain similar calibration. An example is a series of glass tools with known material index and thickness. The tools surfaces radius and thickness can be chosen to simulate distances and behavior of the system when immersed in water and tissue. The focus or minimum spot location can be determined by damaging a sacrificial layer at the desired depth. This sacrificial layer can be a glue or adhesive layer used to bond a reticle or other piece of glass. The minimum spot location may then be related to the tissue breakdown depth location. Minimum spot location or best focus location or breakdown location can be determined as a function of X, Y, and Z coordinates. The X & Y coordinates can be ascertained by the placement of a calibrated scaled reticle at the desired depth. The advantage of such an apparatus is that all the subsystems including the UF, the OCT, the aim, and the video can be calibrated with respect to the independently measured set of depth tools with reticles. The disadvantage is the use of a sacrificial surface such as a cement adhesive coating thereby limiting the number of uses.

Alternative to using the error coefficients as correction factors to the generic or nominal look up tables is to use the error information to re-generate the baseline look up table. The error information can be used to adjust parameters used to generate the original generic LUT. An example is to use the error and compare the fit of the original LUT, then choosing different parameters to reduce this fit error. Parameters that may be adjusted include focal length of lenses, position of optical components, and alignment of optical components. An optical model that is used to generate the generic look up table uses these new parameters to re-compute the LUT. The advantage of this technique is the behavior of the location of the breakdown will follow optical rules and physics as dictated by the simulation constraints. Interpolation and extrapolation beyond anchored data points may be more reasonable. The disadvantage to this technique is that it can be difficult and require expert knowledge in lens design and use of production unfriendly design software.

Figure 12:
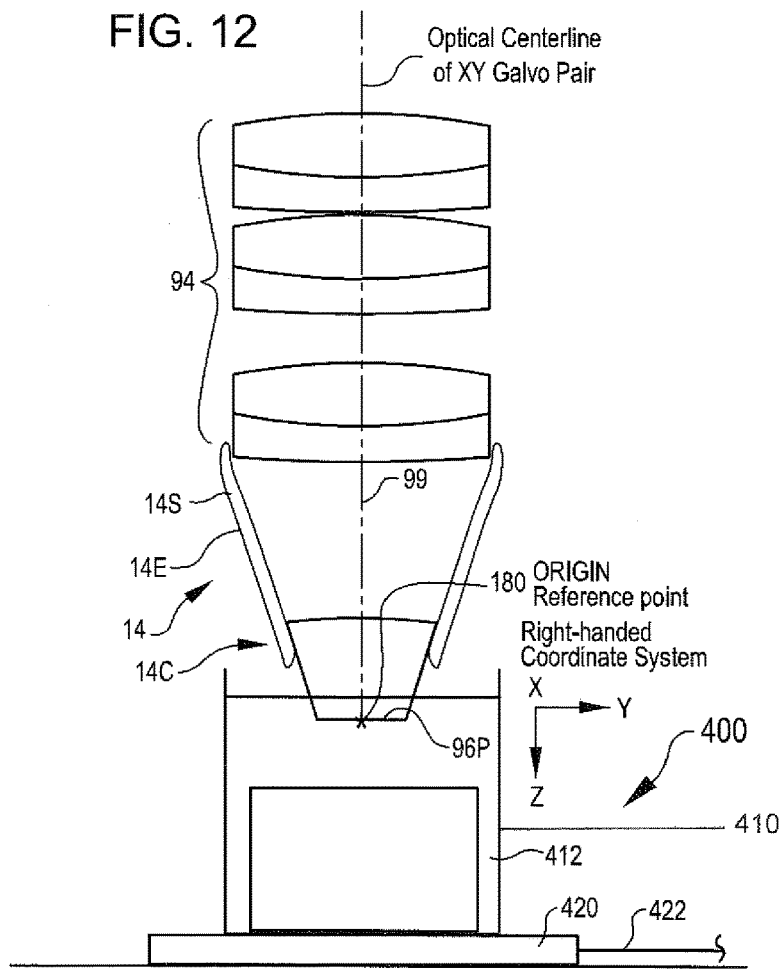
FIG. 12 shows an apparatus to map energy thresholds of a laser system, in accordance with many embodiments.

FIG. 12 shows an apparatus 400 to map energy thresholds of a laser system 2. The apparatus 400 may comprise the container 410, hydrophone 420, patient interface assembly 14, and other components as described herein. The laser system 2 can be programmed to provide a scan pattern at a plurality of depths similar to the depth mapping as described herein. The laser output energy can be adjusted with the attenuator to an amount below the threshold. The laser can be scanned along a plane and the energy increased until optical breakdown is measured at a particular location. The depth Z and lateral location X & Y are known from previous calibrations. These previous calibrations may be conducted as part of the alignment of the optical system. The previously calibrated locations can be determined by using a set of glass tools of material with known index and surface radius so as to simulate X, Y & Z locations in water and tissue. These previous calibrations can be considered coarse or rough and applied in tandem to generic look up tables generated by an optical program using nominal values for beam train components. An example of such a rough calibration is to adjust the offset between the expect focus value of the UF beam on axis to the location of the focus as indicated by the damage to a sacrificial glue layer on a mechanically calibrated tool by adjusting the ZL value of the Z-telescope. A deviation from the expected can be due to deviations from the nominal in regards to placement of the lenses in the Z-telescope, placement of the encoder for the ZL mechanism, and deviations from the minimal collimation conditions of the beam entering the z-telescope. Once optical breakdown has been measured at a particular location, the laser scanning pattern can be controlled so as not to fire further pulses at a location where optical breakdown has been measured. The scan pattern can be repeated and the output energy of the laser adjusted until the optical breakdown energy has been measured at each location of the scan pattern. The depth of the scan pattern can be adjusted further and additional scans at addition depths measured so as to map the optical breakdown threshold over a volume capable of treating a volume of an organ or a plurality of tissues, such as one or more of the cornea, the anterior capsule, the cortex, the nucleus, or the posterior capsule, for example. Once this mapping of threshold value over the volume is accomplished then the calibration of the threshold depth location as described previously can be applied to fine tune the Z location of the cutting. This can be considered a fine adjustment of the calibration procedure and necessary for attaining cut accuracy to below the 100 μm level.

Figure 13A:
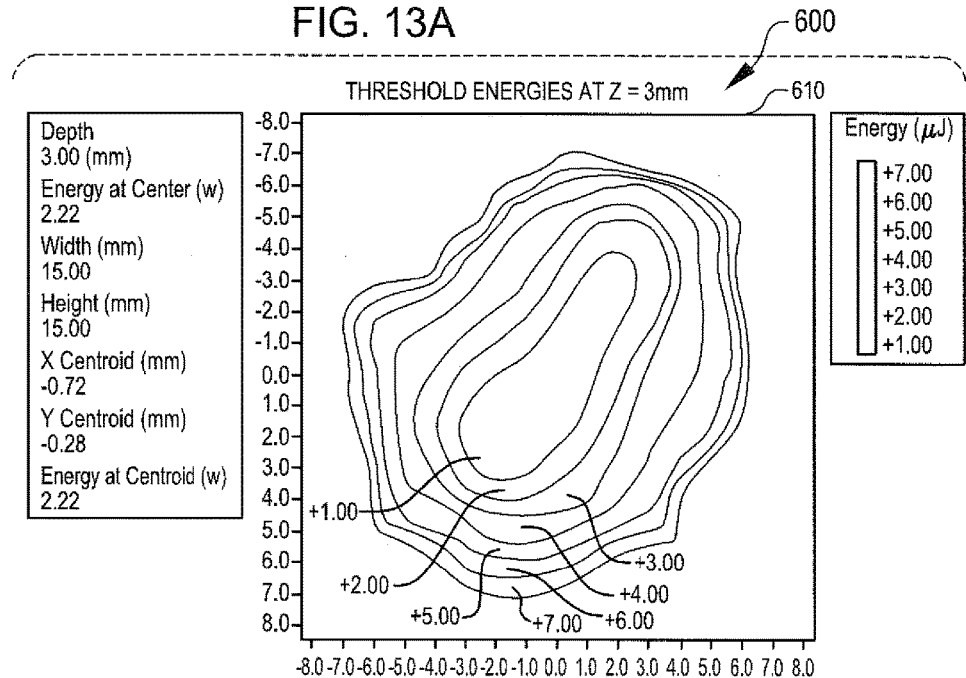
FIG. 13A shows mapped threshold energies corresponding to threshold energies along a plane anterior to an eye, in accordance with many embodiments.

FIG. 13A shows mapped threshold energies 600 corresponding to threshold energies along a plane 610 anterior to an eye. The plane 610 may correspond to a distance of 3 mm from the posterior surface of the optically transmissive structure of the patient interface, for example. The mapped threshold energies comprise a range of values from 1 uJ (micro Joule) to about 7 uJ (micro Joule). The inner central portion comprises the lowest optical breakdown threshold energies, and the outer peripheral portion comprises the highest threshold energies, for example 7 uJ. The focus of the laser beam with system optics can be related to the threshold energy, for example. Other aspects of the system such as reflectance, numerical aperture, prism and beam clipping can be related to changes in the amount of laser energy released to provide the optical breakdown. The calibration as described herein can be capable of accommodating substantial variability in the amount of output laser energy to produce optical breakdown.

Figure 13B:
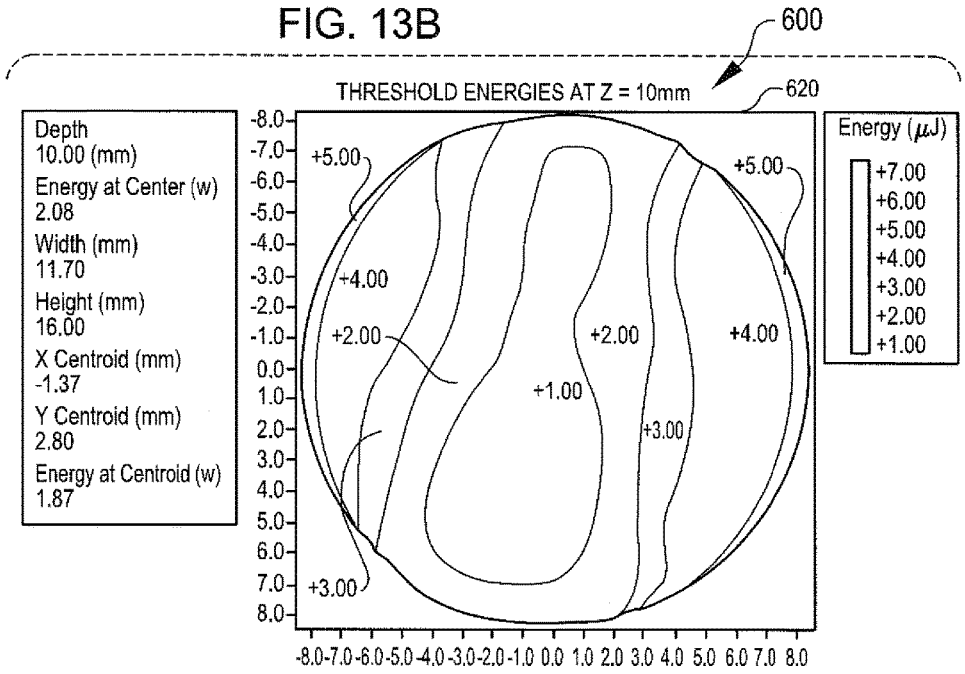
FIG. 13B shows mapped threshold energies corresponding to a plane intersecting a cornea of an eye, in accordance with many embodiments.

FIG. 13B shows mapped threshold energies 600 corresponding to a plane 620 intersecting a cornea of an eye. The plane 620 may correspond to a distance of 10 mm from the posterior surface of the optically transmissive structure of the patient interface, for example. The mapped threshold energies comprise a range of values from 1 uJ (micro Joule) to about 5 uJ (micro Joule). The inner central portion comprises the lowest optical breakdown threshold energies, and the outer peripheral portion comprises the highest threshold energies, for example 5 uJ. The location of the depth in the intermediate zone provides decreased changes in optical breakdown thresholds as compared with at least some locations closer to the system and farther from the system.

Figure 13C:
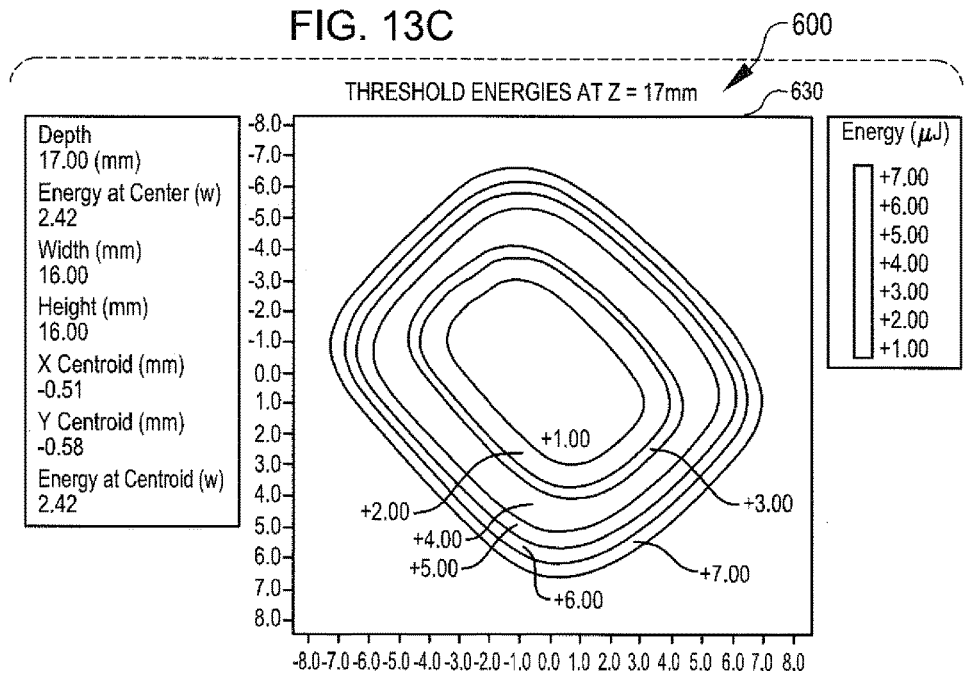
FIG. 13C shows mapped threshold energies corresponding to a plane near a posterior lens capsule, in accordance with many embodiments.

FIG. 13C shows mapped threshold energies 600 corresponding to a plane 630 near a posterior lens capsule. The plane 630 may correspond to a distance of 17 mm from the posterior surface of the optically transmissive structure of the patient interface, for example. The mapped threshold energies comprise a range of values from 1 uJ (micro Joule) to about 7 uJ (micro Joule). The inner central portion comprises the lowest optical breakdown threshold energies, and the outer peripheral portion comprises the highest threshold energies, for example 7 uJ. The location of the depth in the intermediate zone provides decreased changes in optical breakdown thresholds as compared with at least some locations closer to the system and farther from the system.

Figure 14:
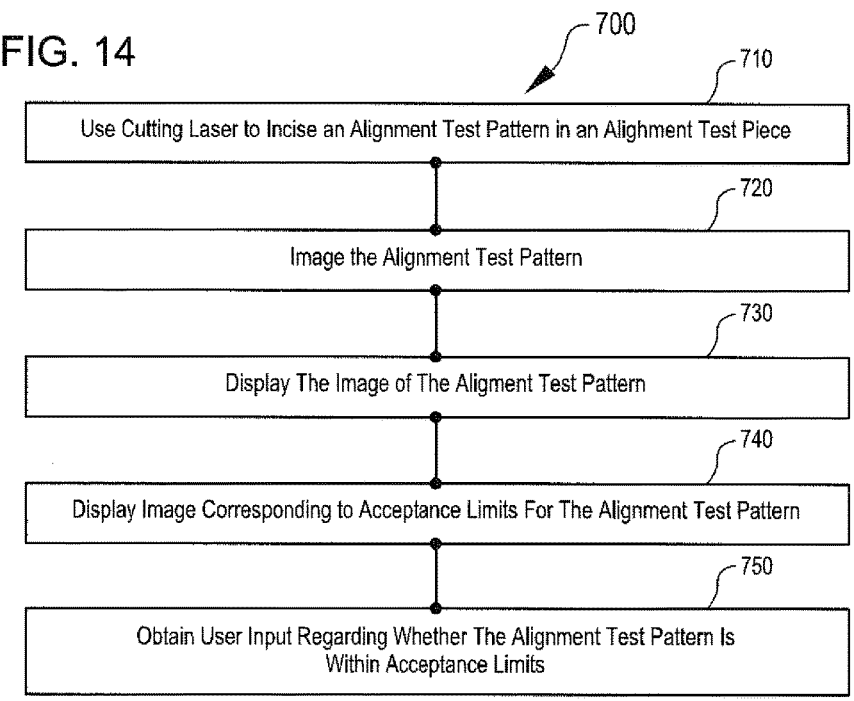
FIG. 14 shows a method of measuring alignment of a laser system, in accordance with many embodiments.

FIG. 14 shows a method 700 of measuring alignment of a laser system.

At a step 710, the cutting laser is used to incise an alignment test pattern in an alignment test piece.

At a step 720, the alignment test pattern is imaged. Imaging can be accomplished for example by the video and the OCT systems.

At a step 730, the image of the alignment test pattern is displayed.

At a step 740, an image corresponding to acceptable tolerance limits is displayed for the alignment test pattern for comparison.

At a step 750, user input is obtained regarding whether the alignment test pattern is within acceptable tolerance limits.

Although the above steps show method 700 of measuring in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 700 may be performed with the circuitry as described herein, for example one or more of the processor or logic circuitry such as the programmable array logic for field programmable gate array. The circuitry may be programmed to provide one or more of the steps of method 700, and the program may comprise program instructions stored on a computer readable memory or programmed steps of the logic circuitry such as the programmable array logic or the field programmable gate array, for example.

Figure 15A:
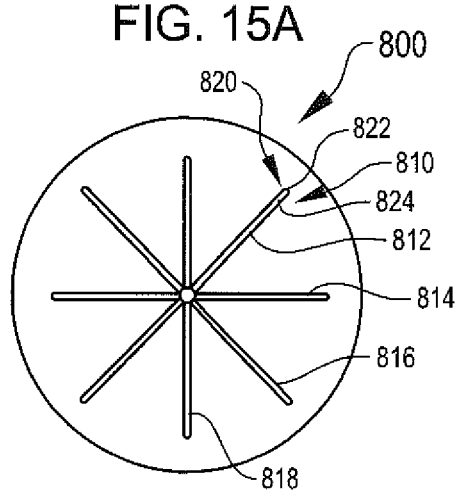
FIG. 15A shows a test pattern to measure alignment of laser system, in accordance with many embodiments.

FIG. 15A shows a test pattern 800 to measure alignment of laser system. The test pattern comprises a cut pattern 810 along a first axis 812, a second axis 814, a third axis 816, and a fourth axis 818. The cut pattern can be overlaid with a video image 820, for example. The video image may comprise a corresponding pattern with tolerances, for example. Alternatively, a calibration card can be provided with the tolerances provided on the card.

The cut can be compared to the reference pattern of the video overlay or card, for example. The cut pattern may comprise an end 824, and the overlay may comprise an end 822. The ends along the axis and the alignment of the cut pattern with the axis can be compared so as to evaluate system alignment.

Figure 15B:
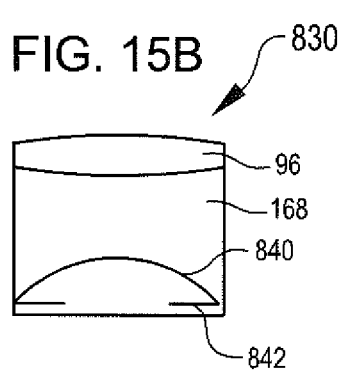
FIG. 15B shows a test eye to measure alignment and energy of the laser system, in accordance with many embodiments.

FIG. 15B shows a test eye 830 to measure alignment and energy of the laser system. The test eye may comprise components similar to a human eye, for example. The test eye may comprise an opaque material 842 that defines a pupil which can be imaged with the system. The test eye 830 comprises a curved surface 840 formed in an optically transparent material having a curvature similar to the cornea. The curvature may comprise a radius within a range from about 6 mm to about 9 mm, for example. A container may contain a liquid 168, for example. The patient interface lens 96 can be placed on top of the test eye 830. The test eye 830 may comprise components of the patient interface assembly 14 as described herein, for example. The test eye 830 can be configured to receive components of the patient interface assembly such as one or more of the support 14S, the docking cone 14C, or the conic extension section 14S, for example.

The laser can be programmed in one or more of many ways to allow the user to test the system. For example, the laser can be programmed to provide a spiral pattern of optical breakdown to transect the surface. When a portion of the treatment has passed from the optically transparent material to above the material, optical breakdown and gassing may occur. The optical breakdown and gassing can be configured to occur during a time of the treatment, for example half way through the treatment. The acceptable tolerances for the observation of the onset of gas can be provided, for example within about 30% of the treatment time to about 70% of the treatment time. The laser system can be configured to determine a pass or fail based on user input, such entering the time when breakdown passed through the surface 840, for example.

Figure 16:
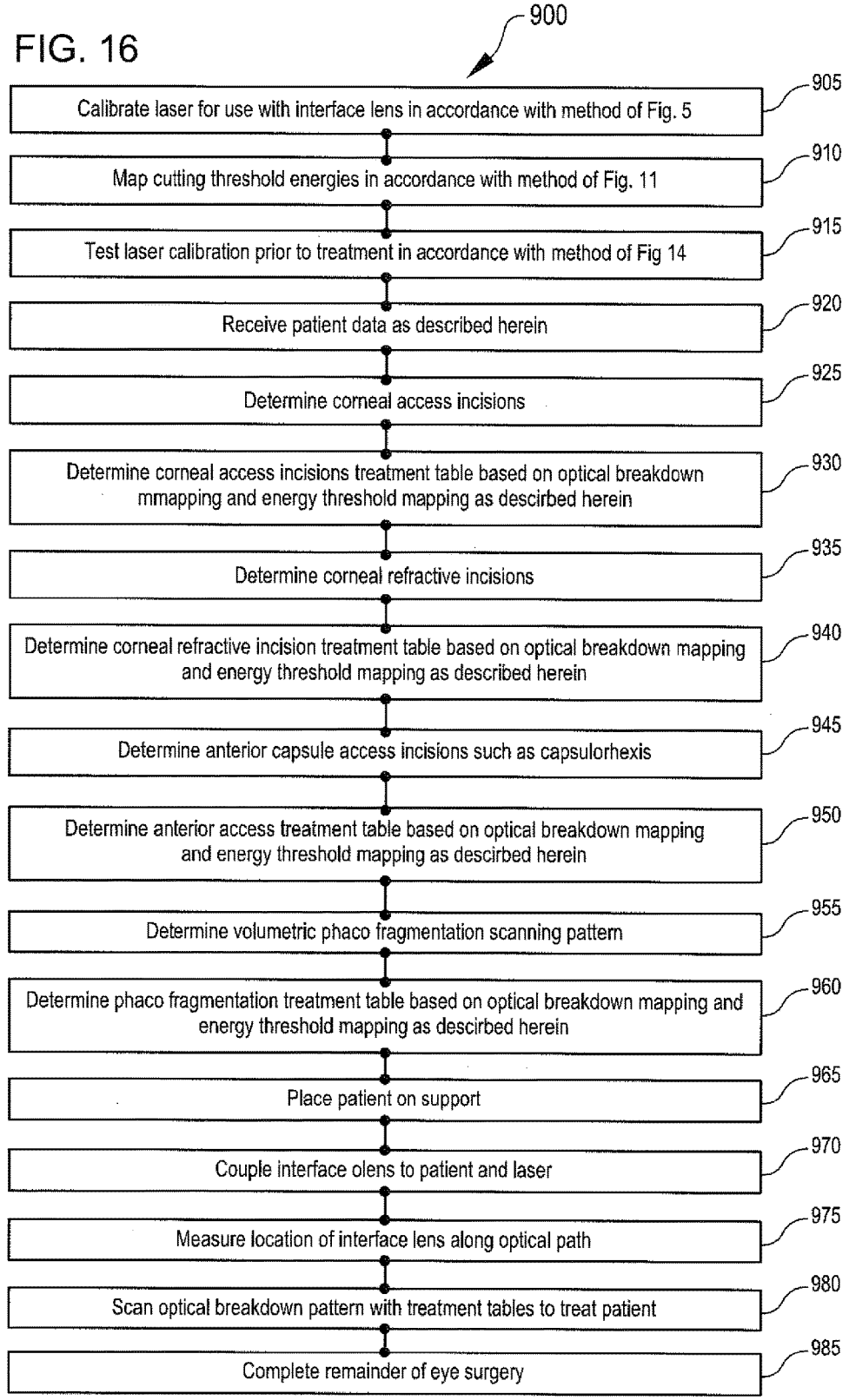
FIG. 16 shows a method of treating a patient, in accordance with many embodiments.

FIG. 16 shows a method 900 of treating a patient, in accordance with many embodiments.

Examples of tissue treatment methods and apparatus suitable for combination in accordance with embodiments as described herein are described in U.S. patent application Ser. No. 12/510,148, filed Jul. 27, 2009, and Ser. No. 11/328,970, filed on Jan. 9, 2006, both entitled "METHOD OF PATTERNED PLASMA-MEDIATED LASER TREPHINATION OF THE LENS CAPSULE AND THREE DIMENSIONAL PHACO-SEGMENTATION", in the name of Blumenkranz et al., the full disclosures of which are incorporated herein by reference.

At a step 905, a laser is calibrated for use with interface lens in accordance with method of FIG. 5.

At a step 910, cutting threshold energies are mapped in accordance with method of FIG. 11.

At a step 915, prior to treatment laser calibration is tested in accordance with method of FIG. 14.

At a step 920, patient data are received as described herein.

At a step 925, corneal access incisions are determined.

At a step 930, a corneal access incision treatment table is determined based on optical breakdown mapping and energy threshold mapping as described herein.

At a step 935, corneal refractive incisions are determined.

At a step 940, a conical refractive incision treatment table is determined based on optical breakdown mapping and energy threshold mapping as described herein.

At a step 945, anterior capsule access incisions are determined such as capsulorhexis.

At a step 950, an anterior access treatment table is determined based on optical breakdown mapping and energy threshold mapping as described herein.

At a step 955, a volumetric phaco fragmentation scanning pattern is determined.

At a step 960, a phaco fragmentation treatment table is determined based on optical breakdown mapping and energy threshold mapping as described herein.

At a step 965, the patient is placed on the support.

At a step 970, the interface lens is coupled to the patient and the laser.

At a step 975, a location of interface lens is measured along the optical path.

At a step 980, an optical breakdown pattern is scanned with treatment tables to treat the patient.

At a step 985, the remainder of eye surgery is completed.

Although the above steps show method 900 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 900 may be performed with the circuitry as described herein, for example one or more of the processor or logic circuitry such as the programmable array logic for field programmable gate array. The circuitry may be programmed to provide one or more of the steps of method 900, and the program may comprise program instructions stored on a computer readable memory or programmed steps of the logic circuitry such as the programmable array logic or the field programmable gate array, for example.

The methods and apparatus as described herein are suitable for combination with one or more components of laser eye surgery systems that are under development or commercially available such as:

an adaptive patient interface is described in Patent Cooperation Treaty Patent Application (hereinafter "PCT") PCT/US2011/041676, published as WO 2011/163507, entitled "ADAPTIVE PATIENT INTERFACE";

a device and method for aligning an eye with a surgical laser are described in PCT/IB2006/000002, published as WO 2006/09021, entitled "DEVICE AND METHOD FOR ALIGNING AN EYE WITH A SURGICAL LASER";

a device and method for aligning an eye with a surgical laser are described in PCT/IB2006/000002, published as WO 2006/09021, entitled "DEVICE AND METHOD FOR ALIGNING AN EYE WITH A SURGICAL LASER";

an apparatus for coupling an element to the eye is described in U.S. application Ser. No. 12/531,217, published as U.S. Pub. No. 2010/0274228, entitled "APPARATUS FOR COUPLING AN ELEMENT TO THE EYE"; and a servo controlled docking force device for use in ophthalmic applications is described in U.S. application Ser. No. 13/016,593, published as U.S. Pub. No. US 2011/0190739, entitled "SERVO CONTROLLED DOCKING FORCE DEVICE FOR USE IN OPHTHALMIC APPLICATIONS".

With the teachings described herein, a person of ordinary skill in the art can modify the above referenced devices to practice many of the embodiments described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. An apparatus to treat an eye, the apparatus comprising:
a pulsed laser to generate pulses of light energy;

an optical delivery system coupled to the laser;
a processor coupled to the pulsed laser and the optical delivery system, the processor configured to generate a treatment table having a plurality of columns including:
columns of input parameters comprising a plurality of three dimensional target locations of the eye, and
columns of output parameters comprising corresponding values of adjustable control parameters of the optical delivery system for directing the pulses of laser energy to the three dimensional target locations of the eye, and
wherein the processor is further configured to adjust the laser beam pulse energy at the plurality of three dimensional target locations of the eye in response to a look up table which maps the plurality of three dimensional target locations of the eye to a corresponding plurality of threshold amounts of laser beam energy to induce optical breakdown at the plurality of three dimensional target locations of the eye.

2. The apparatus of claim 1, wherein the processor is configured to determine the plurality of threshold amounts of laser beam energy to induce optical breakdown at the plurality of three dimensional target locations and in response thereto to create the lookup table.

3. The apparatus of claim 1, wherein the treatment table further includes a header, wherein the header comprises three dimensional coordinates of reference locations of identifiable structures, and values of adjustable control parameters of the optical delivery system for directing the pulses of laser energy to the reference locations.

4. The apparatus of claim 3, wherein the reference locations include a location of the cornea of the eye along a Z axis, a location of the limbus of the eye along an X axis and a location of the limbus of the eye along a Y axis.

5. The apparatus of claim 1, wherein the columns of input parameters in the treatment table include a column of X coordinates, a column of Y coordinates, and a column of Z coordinates of the three dimensional target locations of the eye.

6. The apparatus of claim 5, wherein the optical delivery system includes an X scan mirror to scan the pulsed laser beam to different X coordinates in the eye, a Y scan mirror to scan the pulsed laser beam to different Y coordinates in the eye, and a Z-telescope to direct the pulsed laser beam to different depths in the eye, and wherein the columns of output parameters includes an X scan column of positions of the X-scan mirror, a Y scan column of positions of the Y-scan mirror, and a Z-telescope column of positions of the Z-telescope.

7. An apparatus to treat an eye, the apparatus comprising:
a laser to generate a plurality of laser beam pulses;
an optical delivery system to deliver the plurality of laser beam pulses to a plurality of three dimensional target locations of the eye;
a processor coupled to the laser and the optical delivery system, the processor configured to determine a threshold amount of an output pulse energy of the laser to provide optical breakdown within the eye for each of a plurality of three dimensional target locations of the eye,
wherein the processor is configured to generate a treatment table having a plurality of columns including:
columns of input parameters comprising a plurality of three dimensional target locations of the eye, and
columns of output parameters comprising values of adjustable control parameters of the optical delivery system for directing the pulses of laser energy to the three dimensional target locations of the eye, and
wherein the processor is further configured to adjust the output pulse energy of the laser below the threshold amount for each of the plurality of three dimensional target locations of the eye in order to provide optical breakdown within the eye.

8. The apparatus of claim 7, wherein the treatment table further includes a header, wherein the header comprises three dimensional coordinates of reference locations of identifiable structures, and values of adjustable control parameters of the optical delivery system for directing the pulses of laser energy to the reference locations.

9. The apparatus of claim 8, wherein the reference locations include a location of the cornea of the eye along a Z axis, a location of the limbus of the eye along an X axis and a location of the limbus of the eye along a Y axis.

10. The apparatus of claim 7, wherein the columns of input parameters in the treatment table include a column of X coordinates, a column of Y coordinates, and a column of Z coordinates of the three dimensional target locations of the eye.

11. The apparatus of claim 10, wherein the optical delivery system includes an X scan mirror to scan the pulsed laser beam to different X coordinates in the eye, a Y scan mirror to scan the pulsed laser beam to different Y coordinates in the eye, and a Z-telescope to direct the pulsed laser beam to different depths in the eye, and wherein the columns of output parameters includes an X scan column of positions of the X-scan mirror, a Y scan column of positions of the Y-scan mirror, and a Z-telescope column of positions of the Z-telescope.

12. The apparatus of claim 7, wherein the columns of input parameters in the treatment table include a column of X coordinates, a column of Y coordinates, and a column of Z coordinates of the three dimensional target locations of the eye.

13. The apparatus of claim 12, wherein the optical delivery system includes an X scan mirror to scan the pulsed laser beam to different X coordinates in the eye, a Y scan mirror to scan the pulsed laser beam to different Y coordinates in the eye, and a Z-telescope to direct the pulsed laser beam to different depths in the eye, and wherein the columns of output parameters includes an X scan column of positions of the X-scan mirror, a Y scan column of positions of the Y-scan mirror, and a Z-telescope column of positions of the Z-telescope.

14. An apparatus to treat an eye, the apparatus comprising:
a laser to generate a plurality of laser beam pulses;
an optical delivery system comprising a movable lens to focus the plurality of laser beam pulses to a plurality of depth locations of the eye;
a patient interface to couple the optical delivery system to the eye, the patient interface comprising an interface lens having an anterior surface and a convexly curved posterior surface; and
a processor configured to adjust the movable lens to maintain focus of the laser beam pulses at the plurality of depth locations of the eye based on a measured location of the interface lens and mapped locations of the eye,
wherein the processor is configured to generate a treatment table having a plurality of columns including:
columns of input parameters defining a plurality of three dimensional target locations of the eye, and columns of output parameters comprising values of adjustable control parameters of the optical delivery system for directing the pulses of laser energy to the three dimensional target locations of the eye, and wherein the processor is further configured to adjust the laser beam pulse energy at the plurality of three dimensional target locations of the eye in response to a look up table which maps the plurality of three dimensional target locations of the eye to a corresponding plurality of threshold amounts of laser beam energy to induce optical breakdown at the plurality of three dimensional target locations of the eye.

15. The apparatus of claim 14, wherein the treatment table further includes a header, wherein the header comprises three dimensional coordinates of reference locations of identifiable structures, and values of adjustable control parameters of the optical delivery system for directing the pulses of laser energy to the reference locations.

16. The apparatus of claim 15, wherein the reference locations include a location of the cornea of the eye along a Z axis, a location of the limbus of the eye along an X axis and a location of the limbus of the eye along a Y axis.

* * * * *